(12) United States Patent
Holcomb

(10) Patent No.: US 6,776,753 B1
(45) Date of Patent: *Aug. 17, 2004

(54) METHOD AND APPARATUS FOR TREATING PAIN WITH THERAPEUTIC MAGNETS

(75) Inventor: Robert Ray Holcomb, Nashville, TN (US)

(73) Assignee: Holcomb Healthcare Services, LLC, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/605,604

(22) Filed: Jun. 28, 2000

Related U.S. Application Data

(60) Provisional application No. 60/141,364, filed on Jun. 28, 1999.

(51) Int. Cl.$^7$ ................................................ A61N 1/00
(52) U.S. Cl. ......................................................... 600/15
(58) Field of Search ........................................ 600/9–15

(56) References Cited

U.S. PATENT DOCUMENTS

| | | | | | |
|---|---|---|---|---|---|
| 3,921,620 | A | * | 11/1975 | Nakayama | 600/15 |
| 4,587,956 | A | * | 5/1986 | Griffin et al. | 600/15 |
| 5,707,333 | A | * | 1/1998 | Bakst | 600/15 |
| 5,782,743 | A | * | 7/1998 | Russell | 600/15 |
| 6,042,531 | A | * | 3/2000 | Holcomb | 600/13 |

FOREIGN PATENT DOCUMENTS

| | | | | |
|---|---|---|---|---|
| WO | 93/24175 | * | 12/1993 | 600/15 |

* cited by examiner

*Primary Examiner*—John P. Lacyk
(74) *Attorney, Agent, or Firm*—Garvey, Smith, Nehrbass & Doody, L.L.C.; Gregory C. Smith

(57) ABSTRACT

A method and system of placement of a magnetic field flux field generator in fitment which creates a specific effect of three dimensional field gradient to alter the charge distribution on living membranes in order to establish normal physiological functioning of damaged tissue.

4 Claims, 27 Drawing Sheets

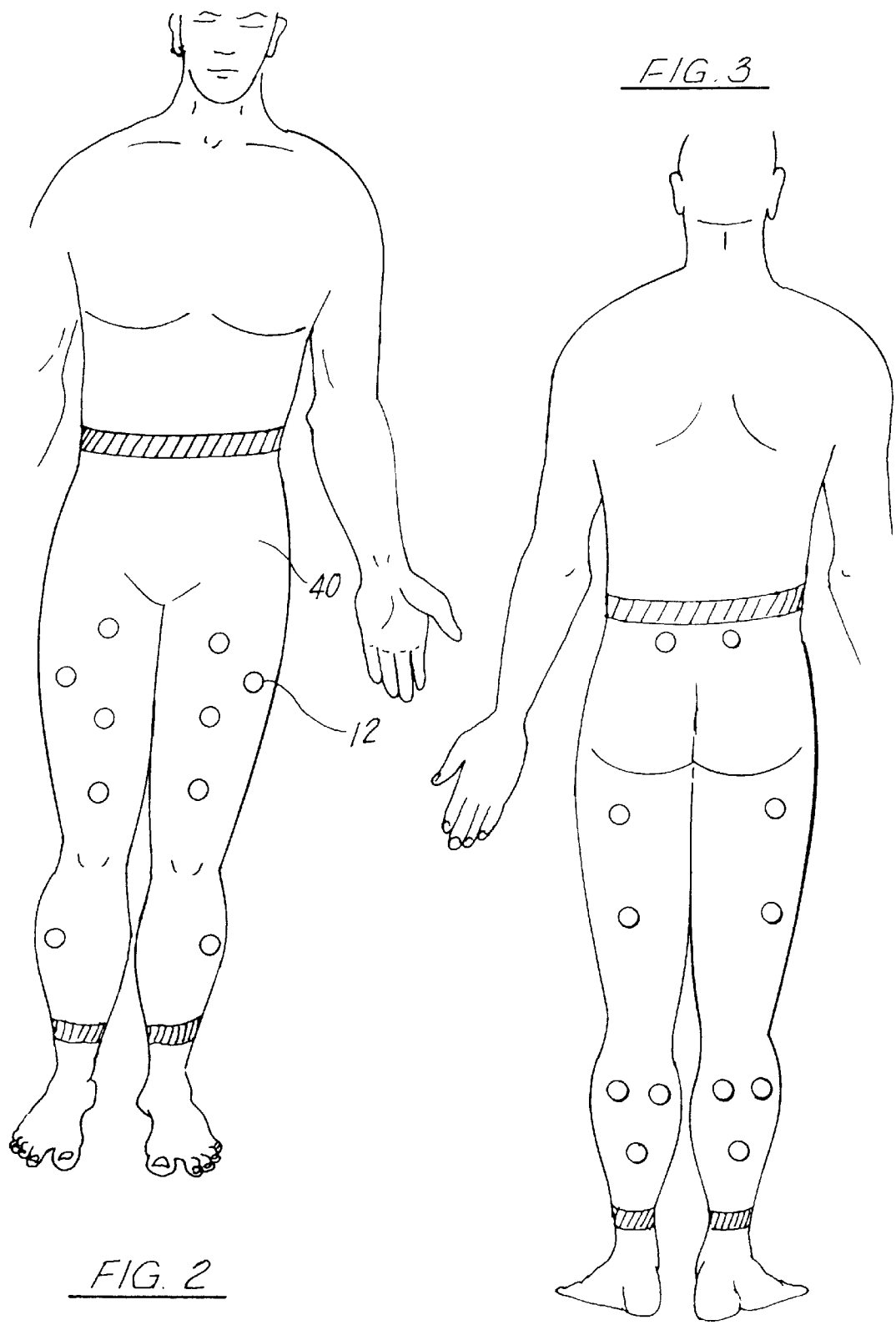

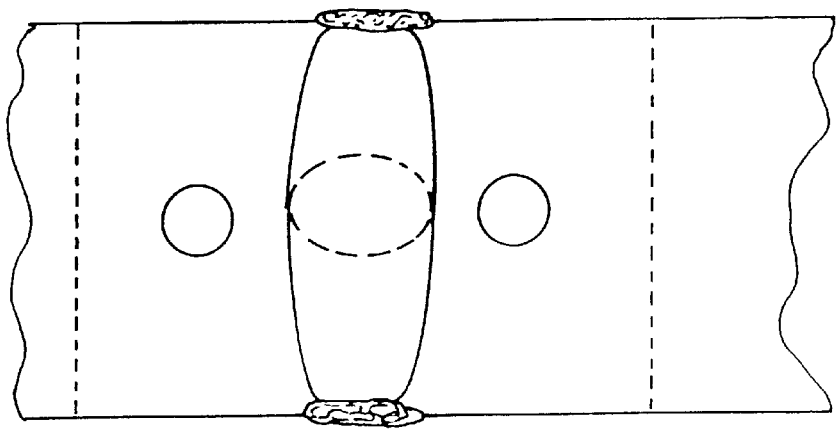
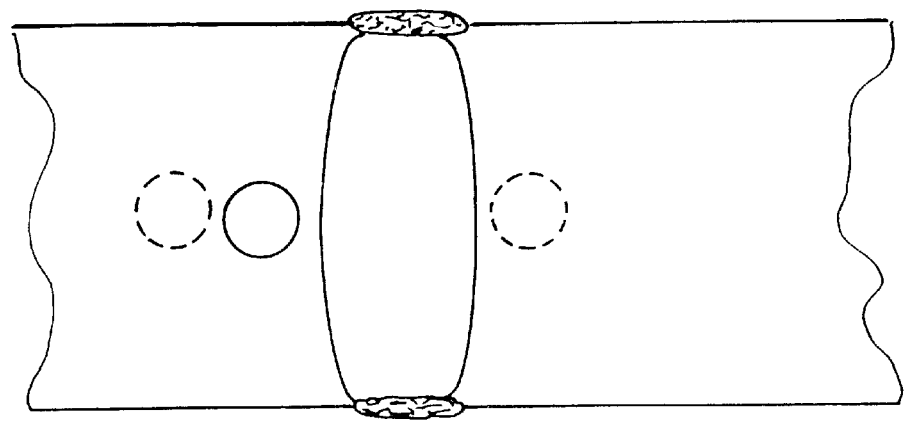
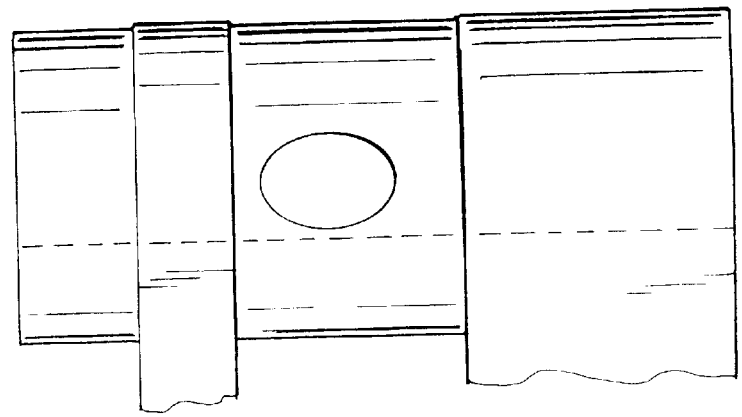
FIG. 22

METHOD AND APPARATUS FOR TREATING PAIN WITH THERAPEUTIC MAGNETS

This application claims priority of provisional patent application 60/141,364, issued as U.S. Pat. No. 6,205,356, filed Jun. 28, 1999, issued as U.S. Pat. No. 6,280,376.

TECHNICAL FIELD

The present invention is related to methods and apparatus for the treatment of pain using magnets and magnetic fields. It is a continuation in part of U.S. Pat. No. 5,941,902 (Continuous Pulse, non-modulated, non-burst mode nerve stimulator and method of applying same), PCT/US98/18967 (Method and apparatus for altering the charge distribution upon living membranes with functional stabilization of the membrane physical & electrical integrity, and provisional application No. 60/141,364).

BACKGROUND OF THE INVENTION

Magnetic devices are known to be effective in treating pain. Proper magnetic fields are believed to inhibit the flow of calcium and sodium ions in the cell membranes of nerves. Accordingly, the transmission of pain is likewise inhibited as well as the stabilization of other cellular dysfunctions such as abnormal fluid transport. Magnetic devices, which produce a magnetic field having a specific three-dimensional gradient in the magnetic flux field, are particularly effective in inhibiting pain. Magnetic devices not producing flux fields with the specific gradients are not effective in relieving pain.

Also, it is important that a magnetic device or a plurality of magnetic devices be properly positioned relative to nerves, muscles, tendons, and ligaments for the initiation and/or inhibition of nerve transmission. Without use of proper magnetic devices or without proper placement of the magnetic devices, magnetic devices are ineffective in relieving pain and improvement of either dysfunction. The present invention overcomes deficiencies in prior use and placement of magnetic devices to provide particularly effective pain and discomfort relief.

SUMMARY OF INVENTION

The present invention includes the use of particularly effective magnetic devices, which are positioned in specified locations on a user's body. The locations were determined by inventive discovery and knowledge of the anatomy and physiology of the body part and its interaction with the specific flux field. The magnetic devices may be applied to the user's body using adhesives, such as double-sided tapes, or positioned using fitments such as elastic wraps, seat cushions, comforters, wristbands, or other carriers for magnets. Preferably, the magnetic device used is the device shown and described in U.S. Pat. Nos. 5,312,321; 5,941,902 and pending PCT/US98/18967, the disclosure of which is hereby incorporated by reference. The device includes four magnet bodies having alternating magnetic poles. The vertices of the magnet bodies form a quadrilateral shape.

The magnetic devices are ideally positioned over specific nerves, muscles and ligaments or other body structures. The specific position has been determined through clinical studies, experience and a scientific knowledge of the interaction of these fields with the body tissues. The positioning for the relief of pain for specific conditions is shown in the attached figures.

BRIEF DESCRIPTION OF THE DRAWINGS

FIGS. 2 and 3 show front and rear views of a user wearing a pair of athletic tights containing magnetic devices affixed therein;

Flux Generator, shows various placements of magnetic devices relative to a user's body for the treatment of pain and/or discomfort.

Figure 7:
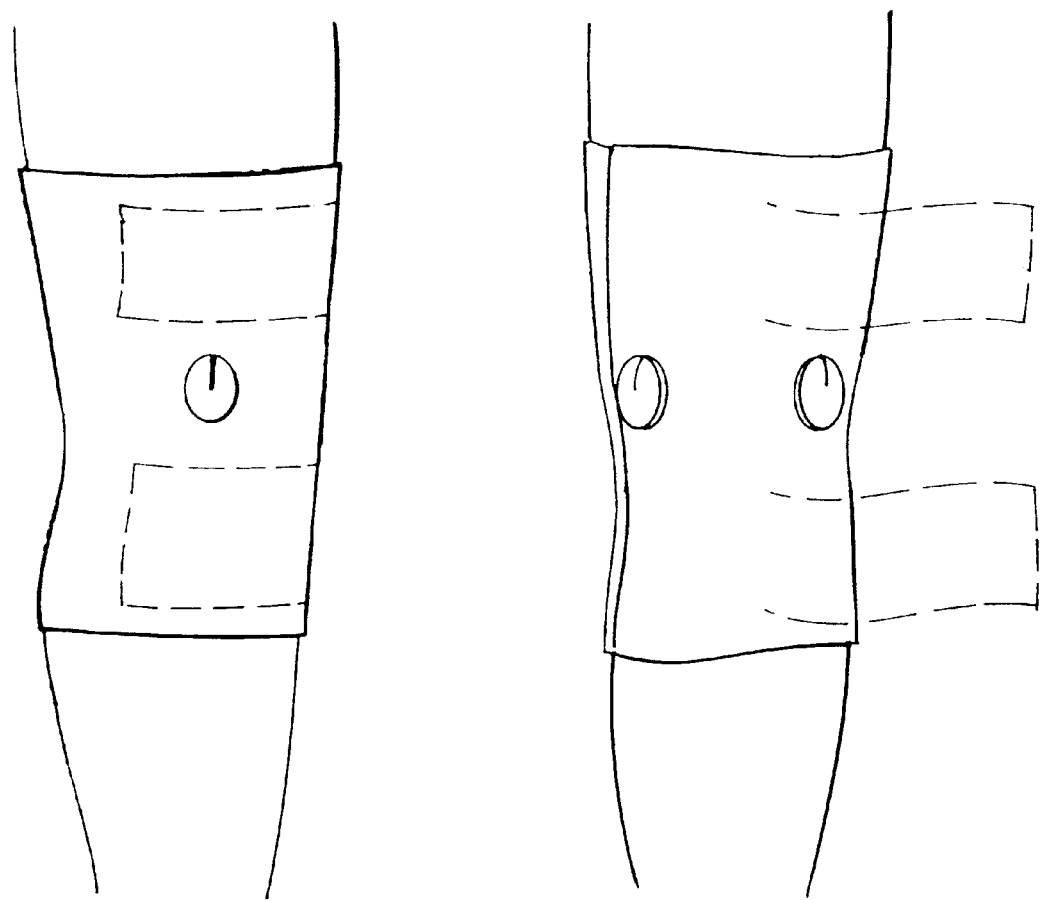
Figure 8:
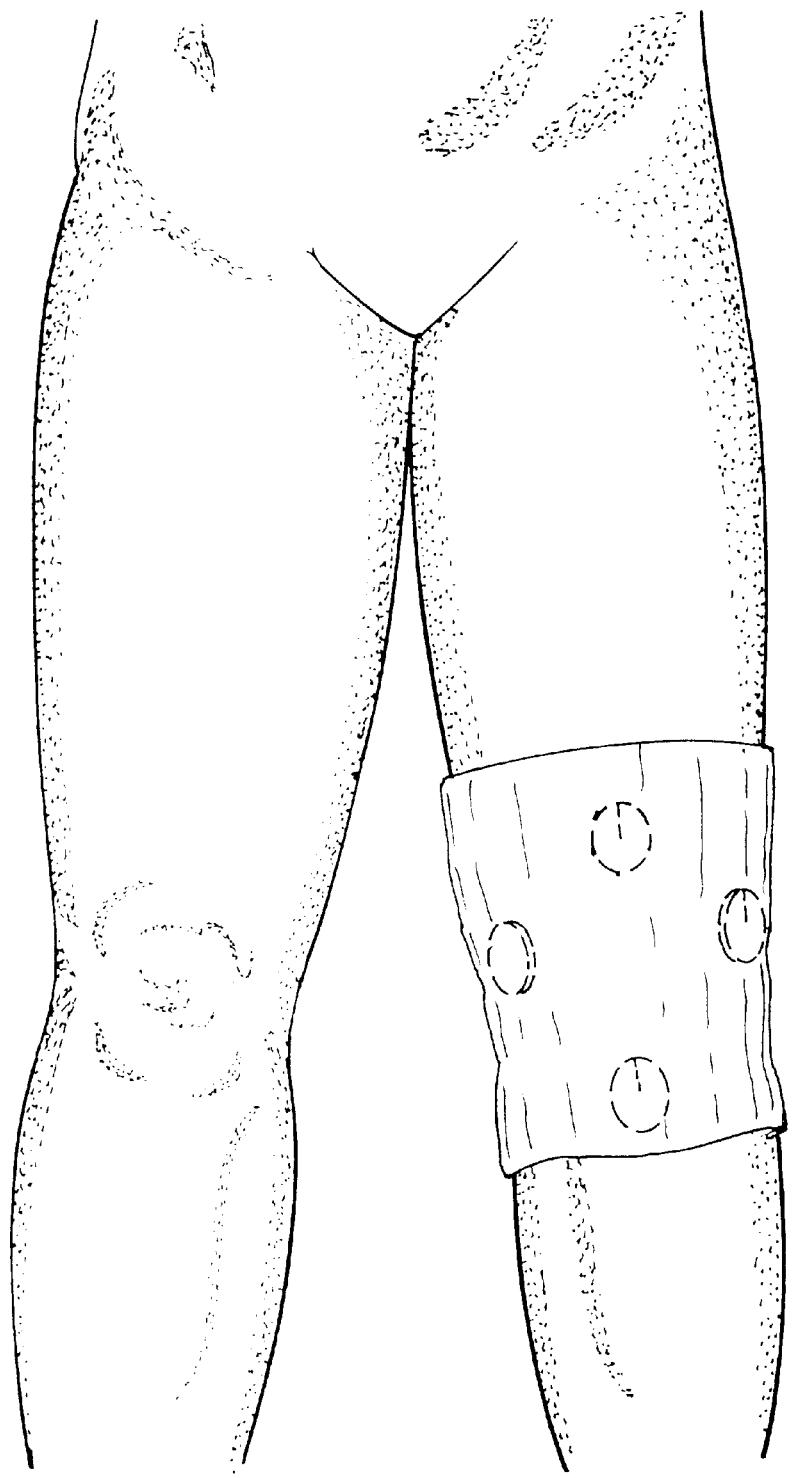
Figure 9:
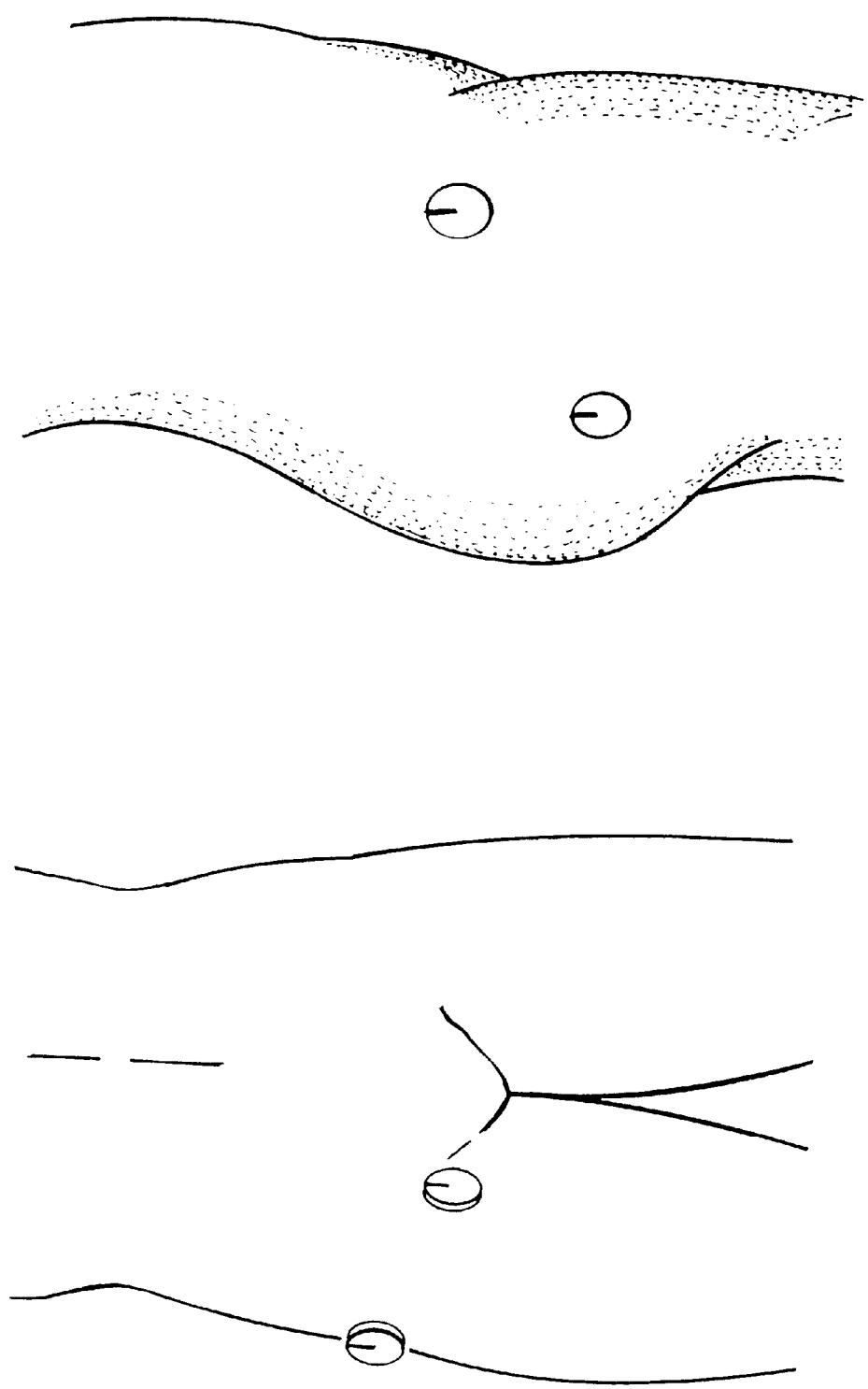
Figure 10A:
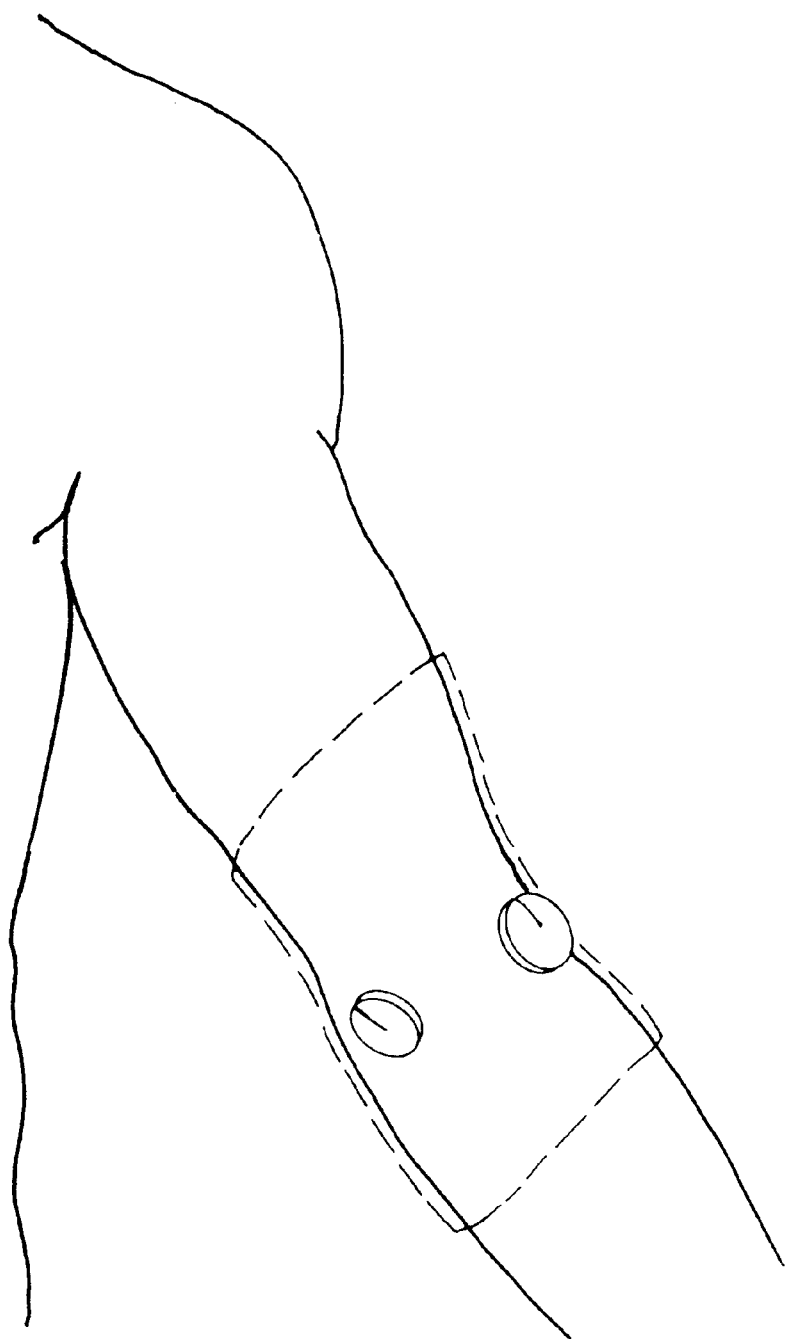
Figure 10B:
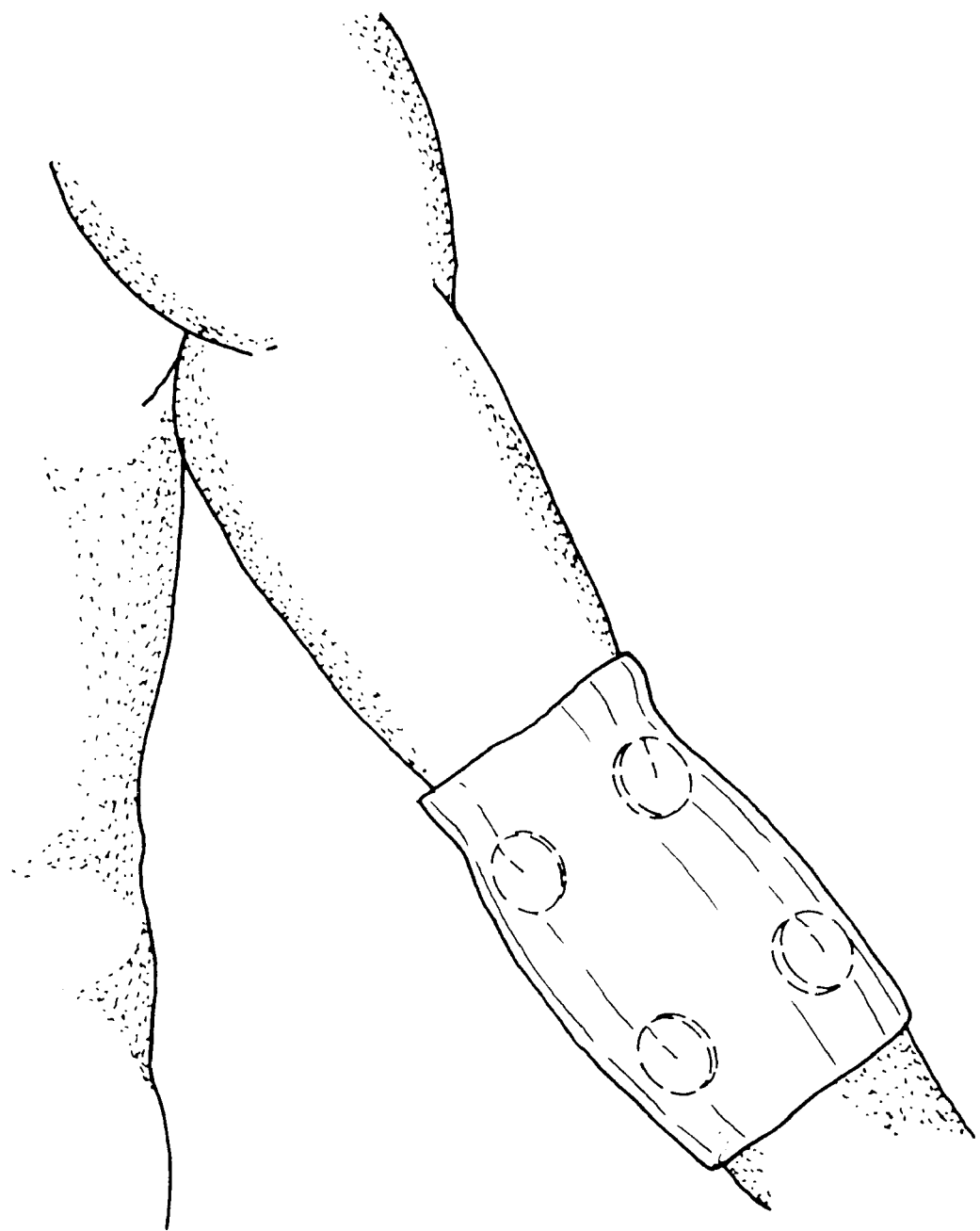
Figure 11A:
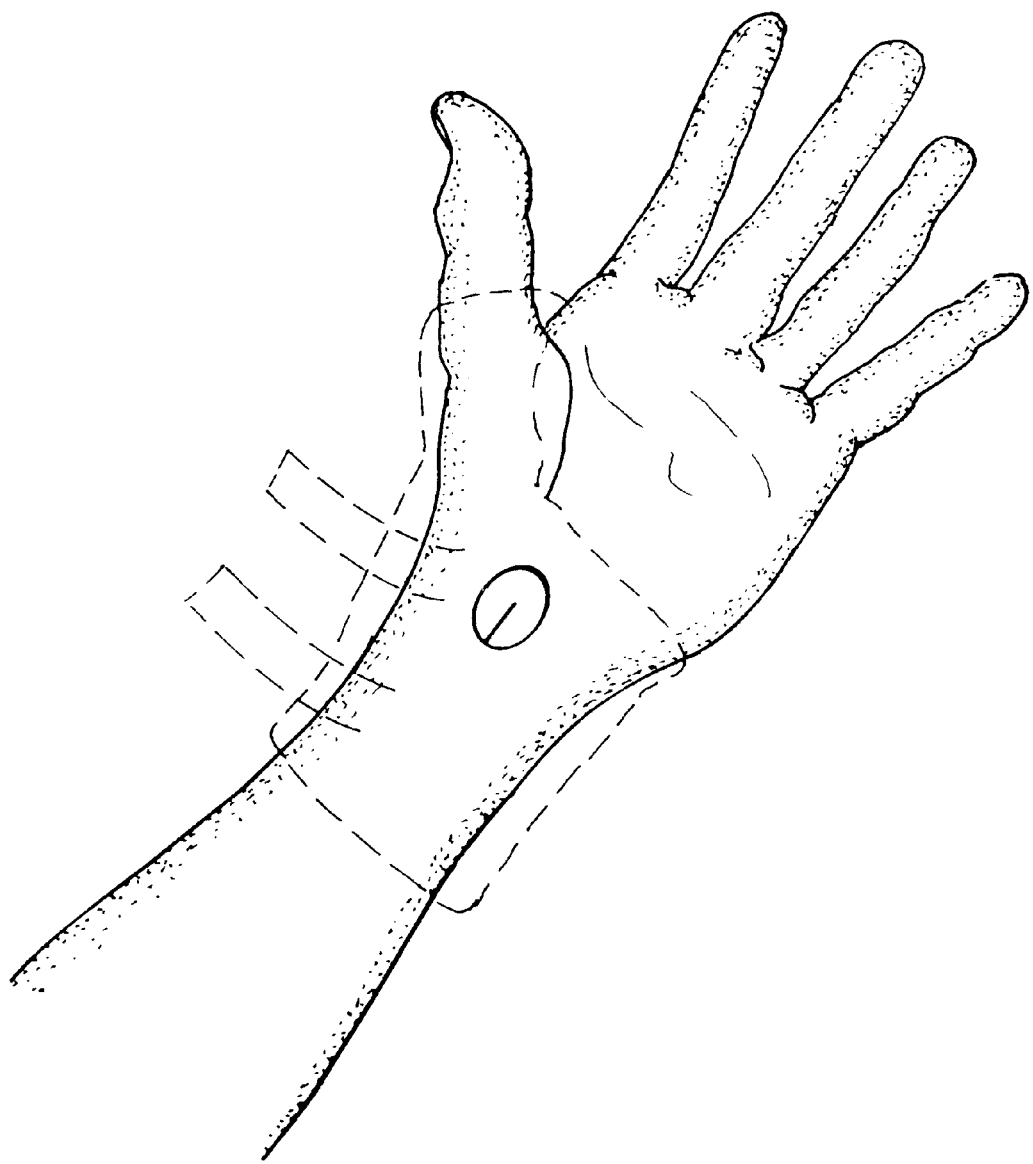
Figure 11B:
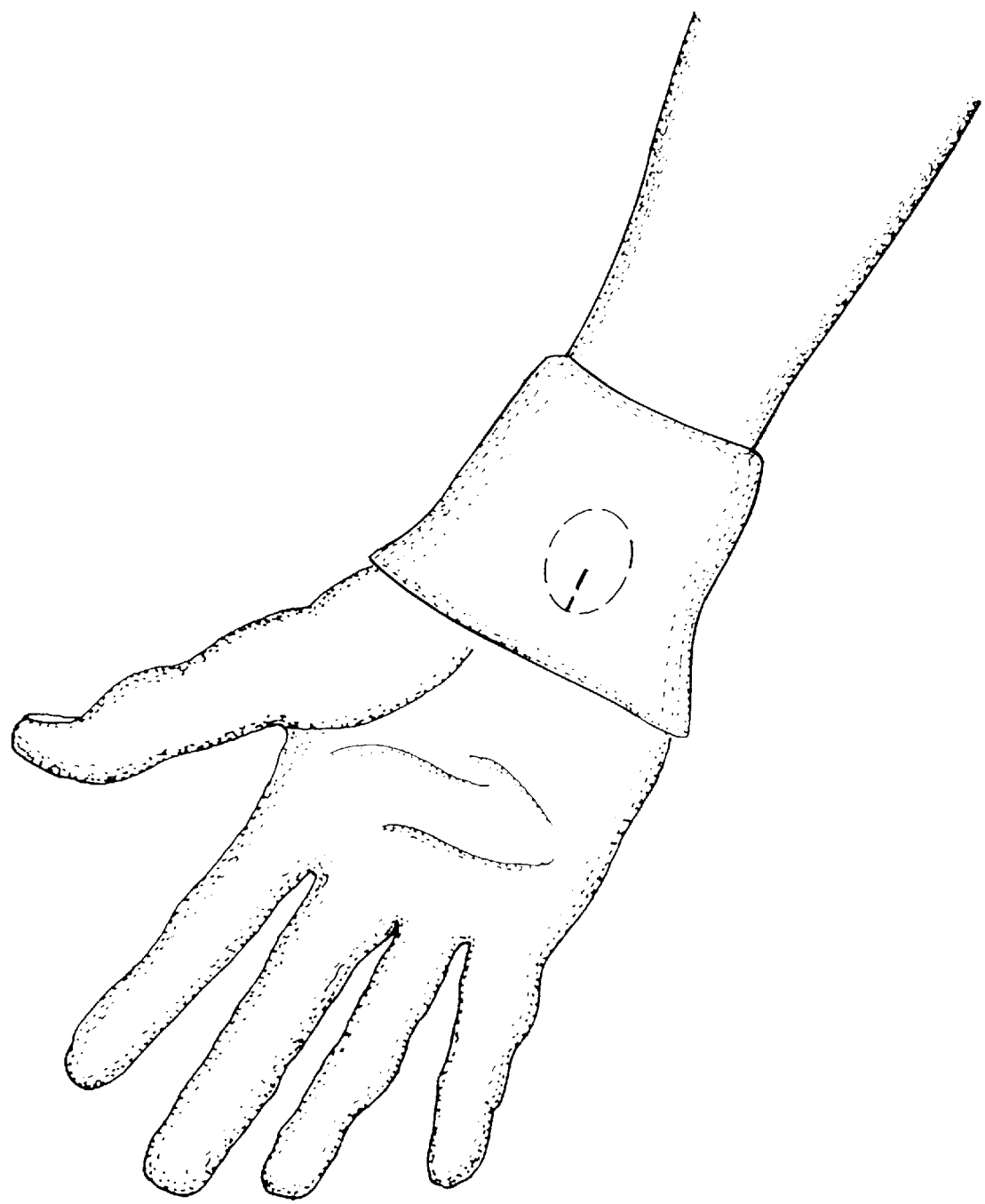
Figure 11C:
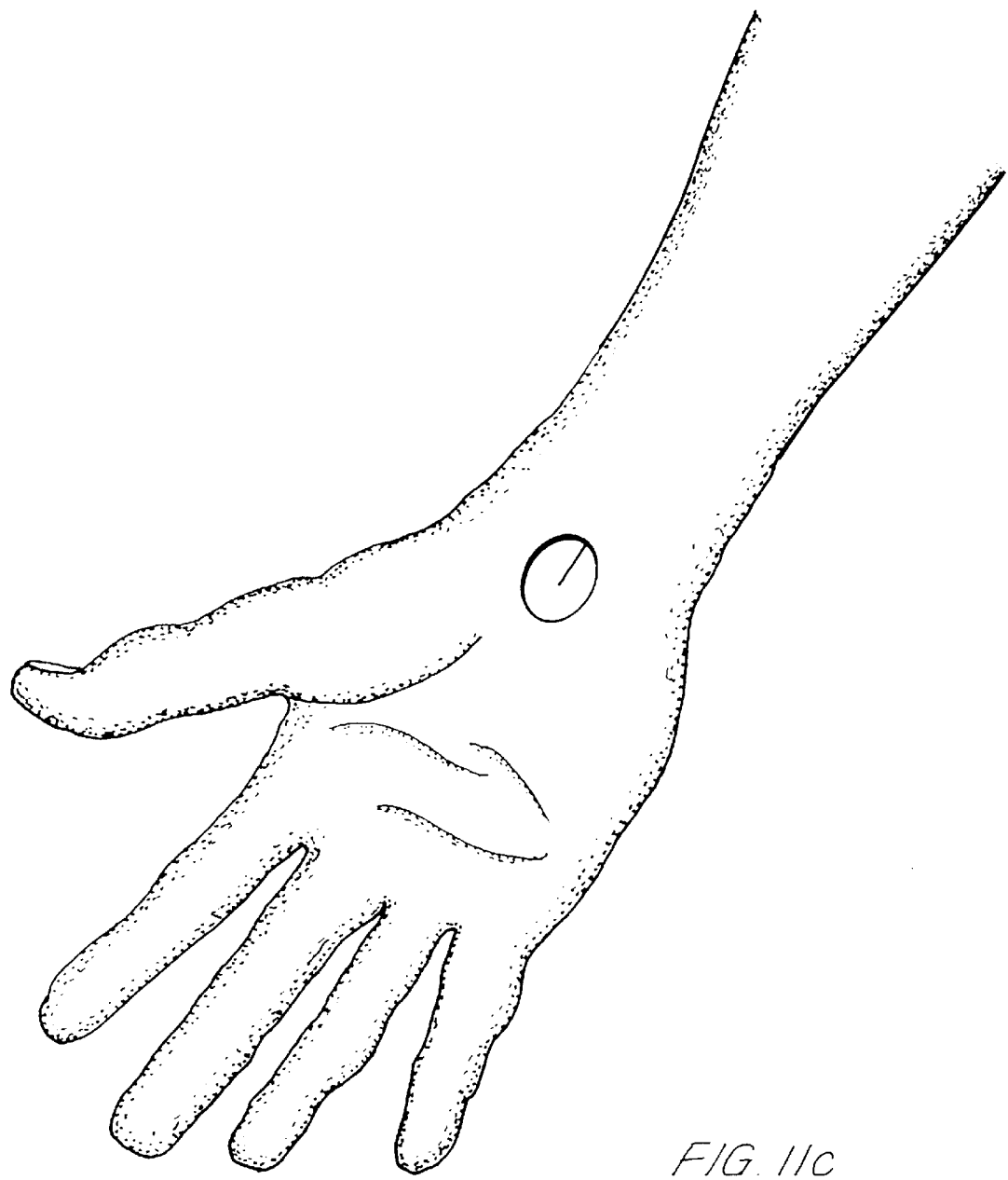
Figure 12:
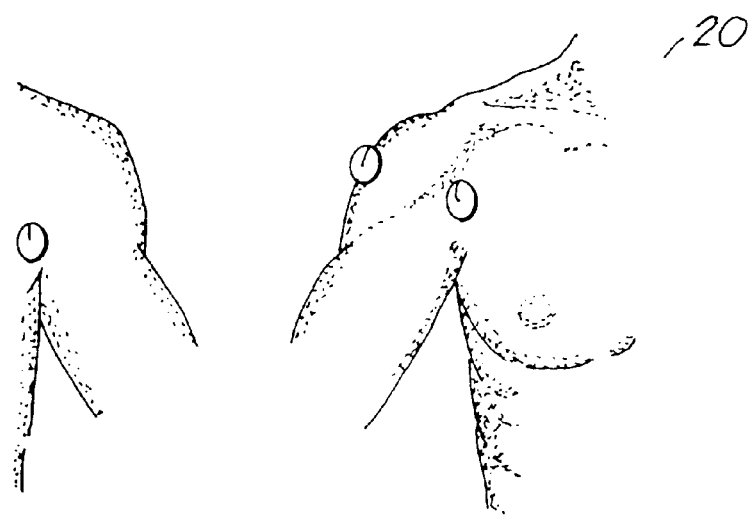
Figure 13:
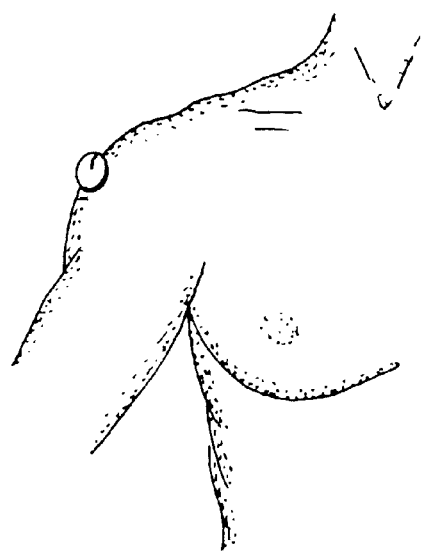
Figure 14:
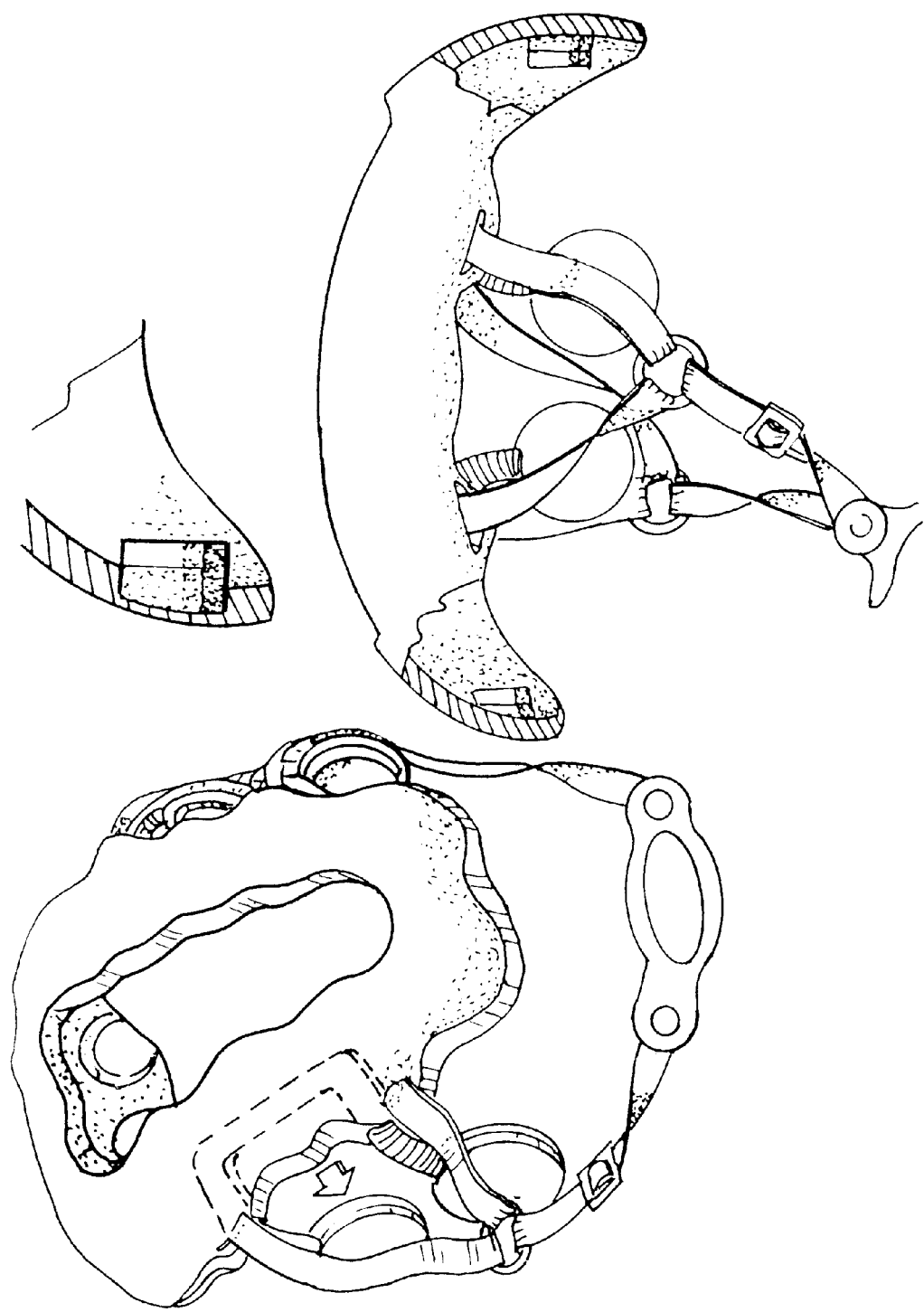
Figure 15:
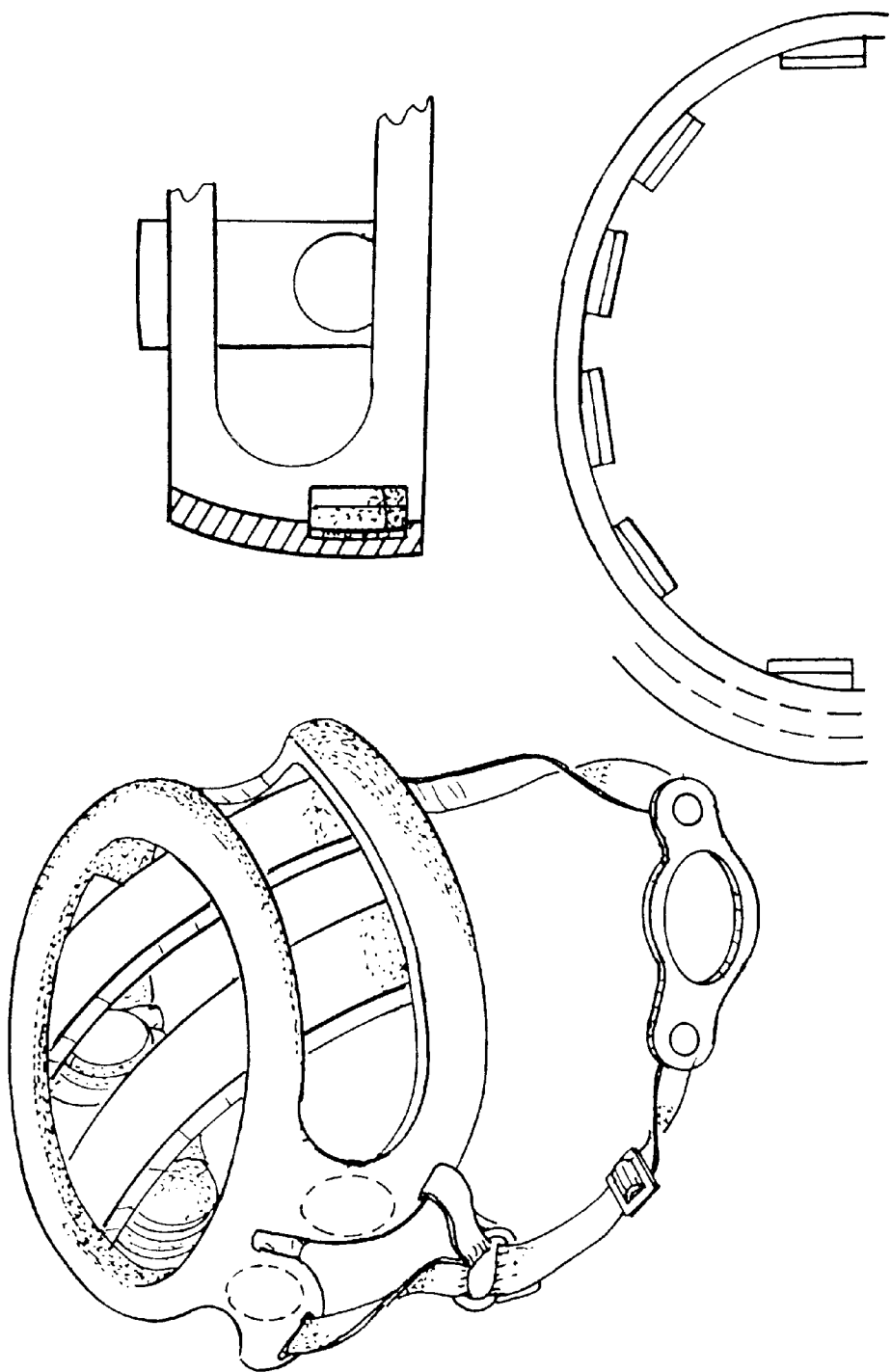
Figure 16:
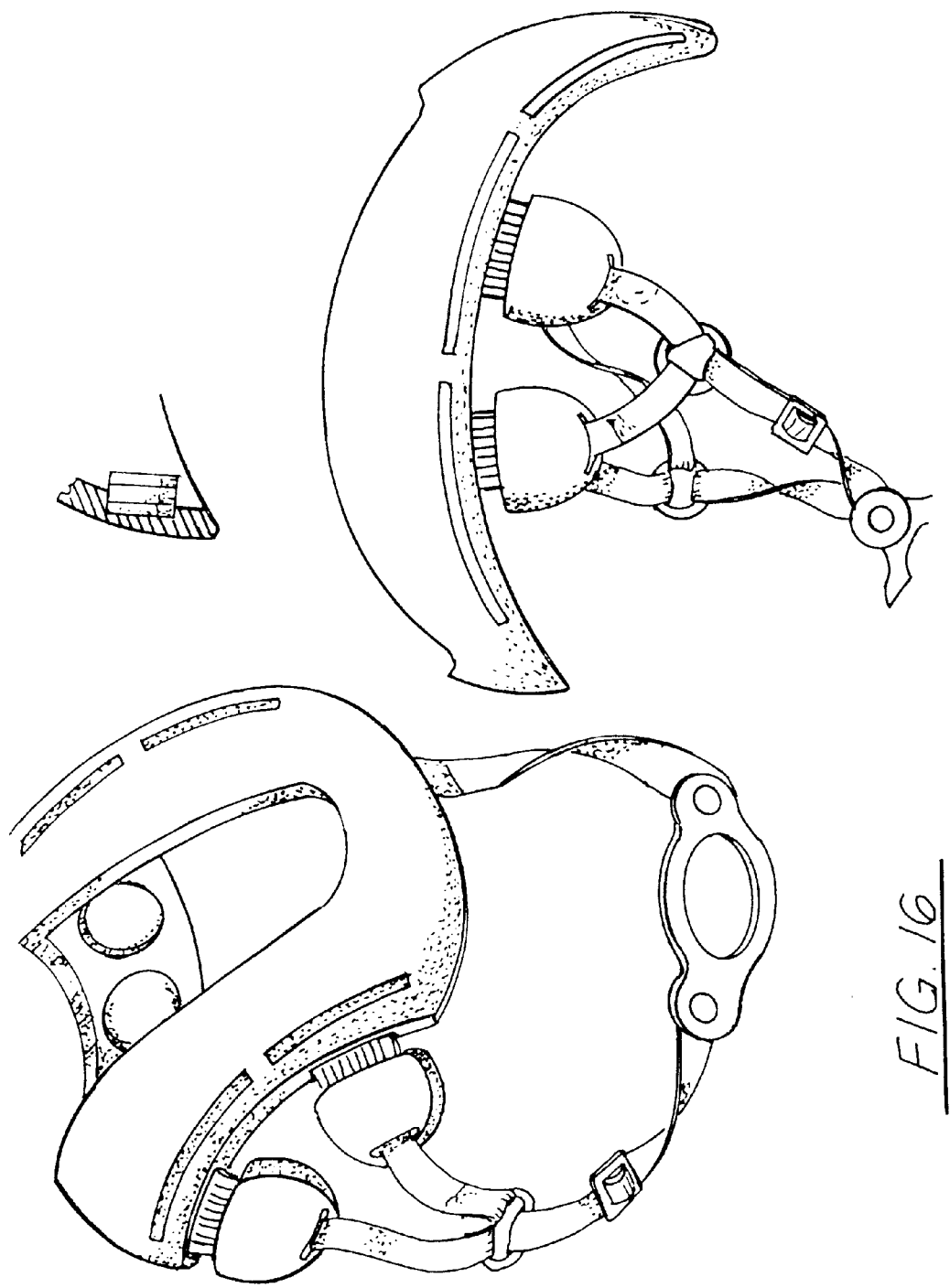
Figure 17:
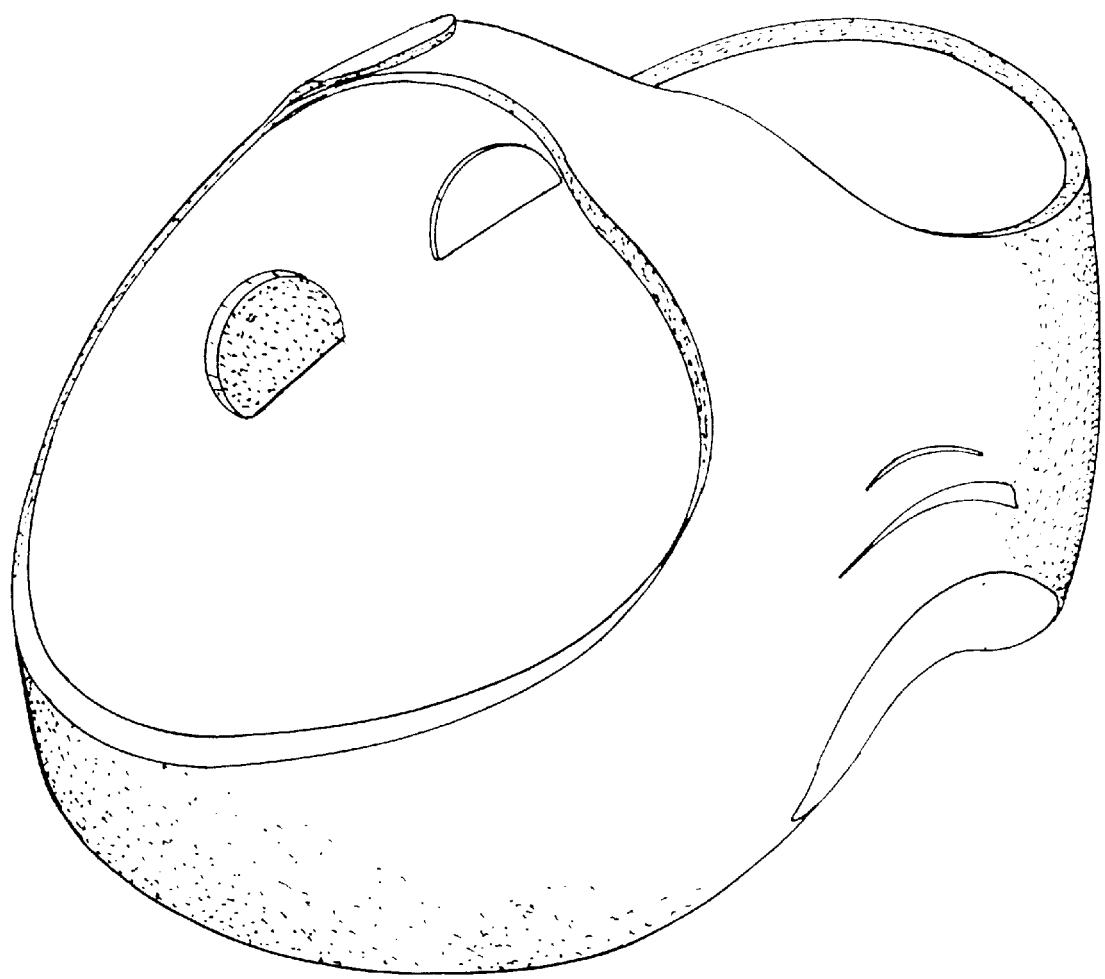
Figure 18:
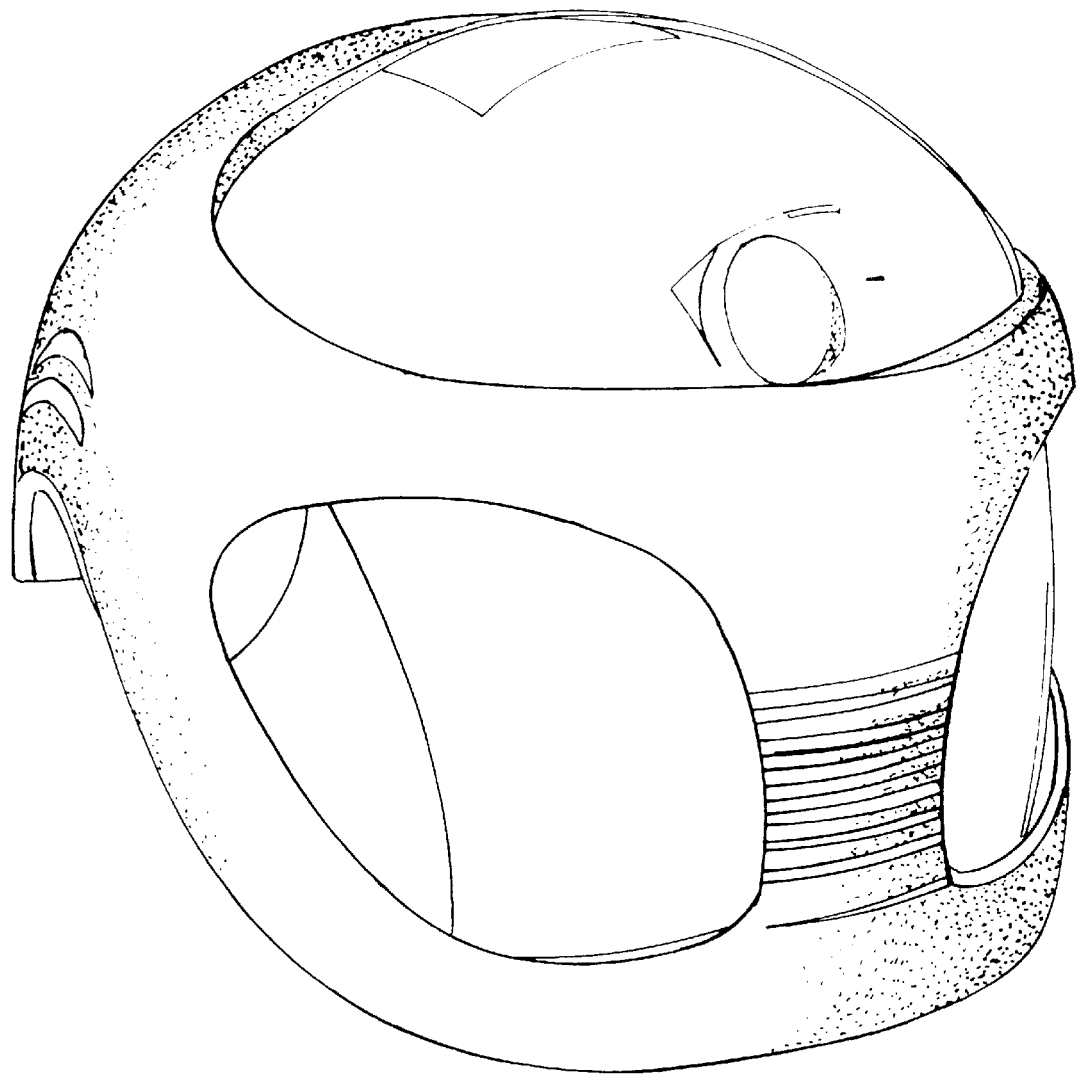
Figure 19:
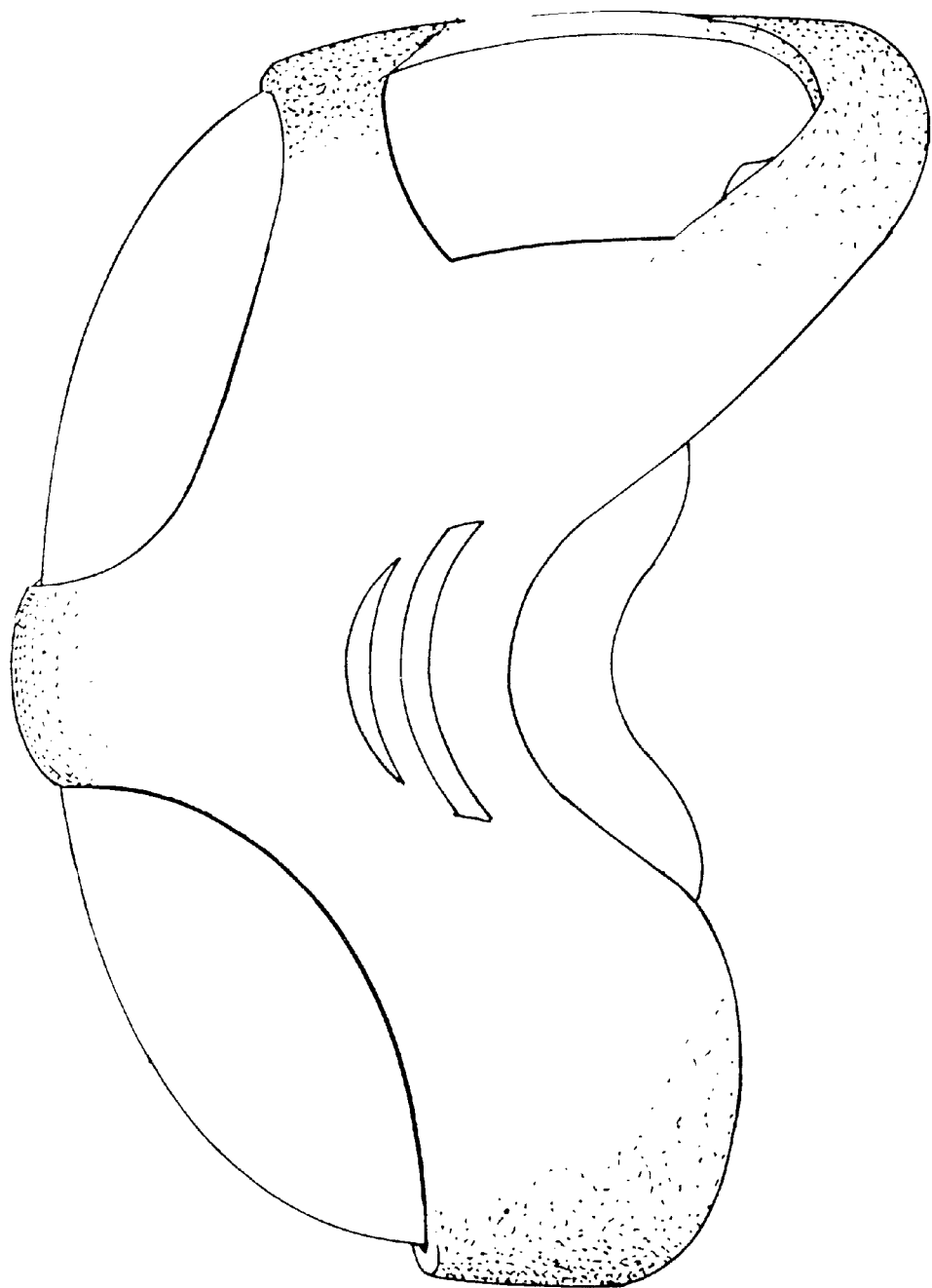
Figure 20:
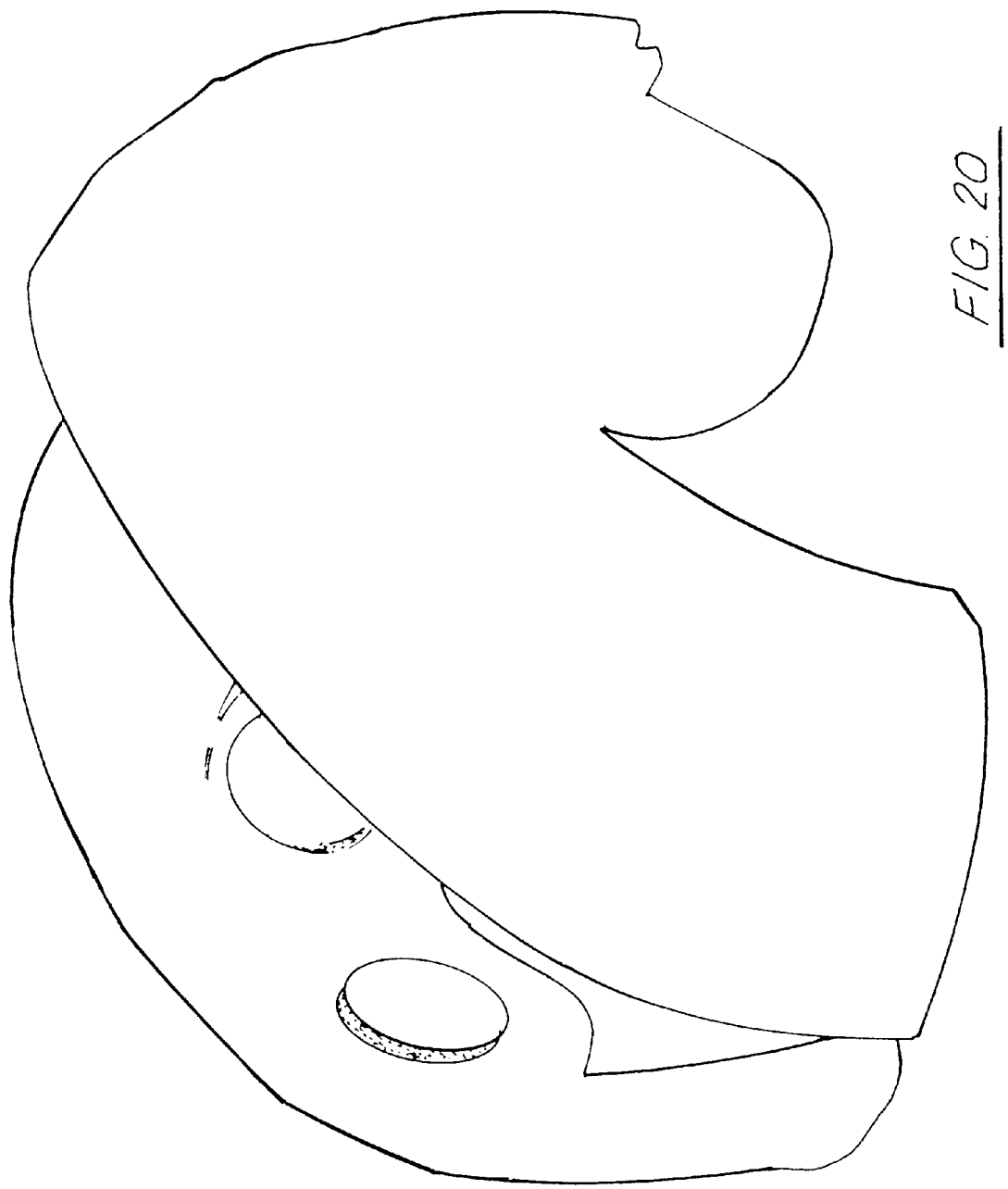
Figure 21:
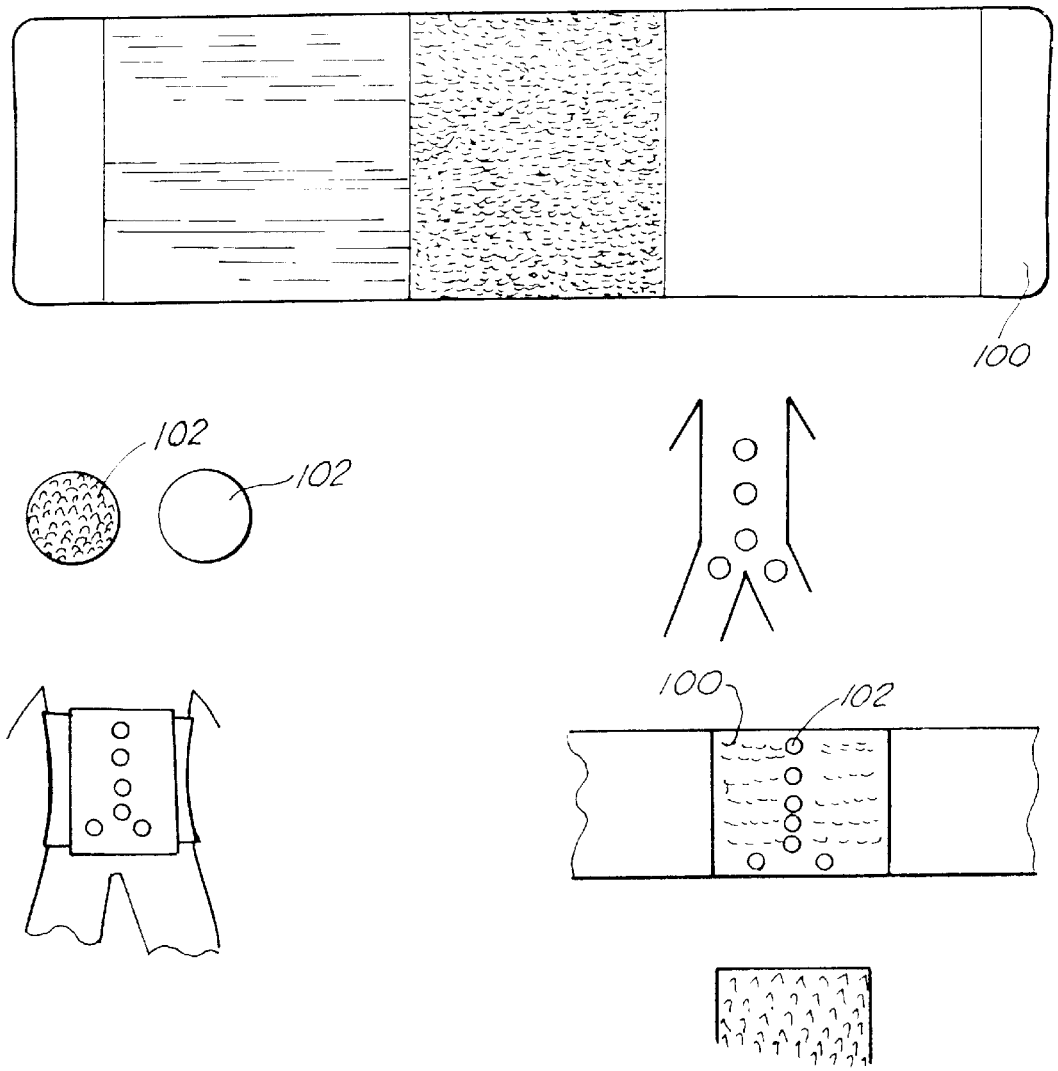
Figure 23:
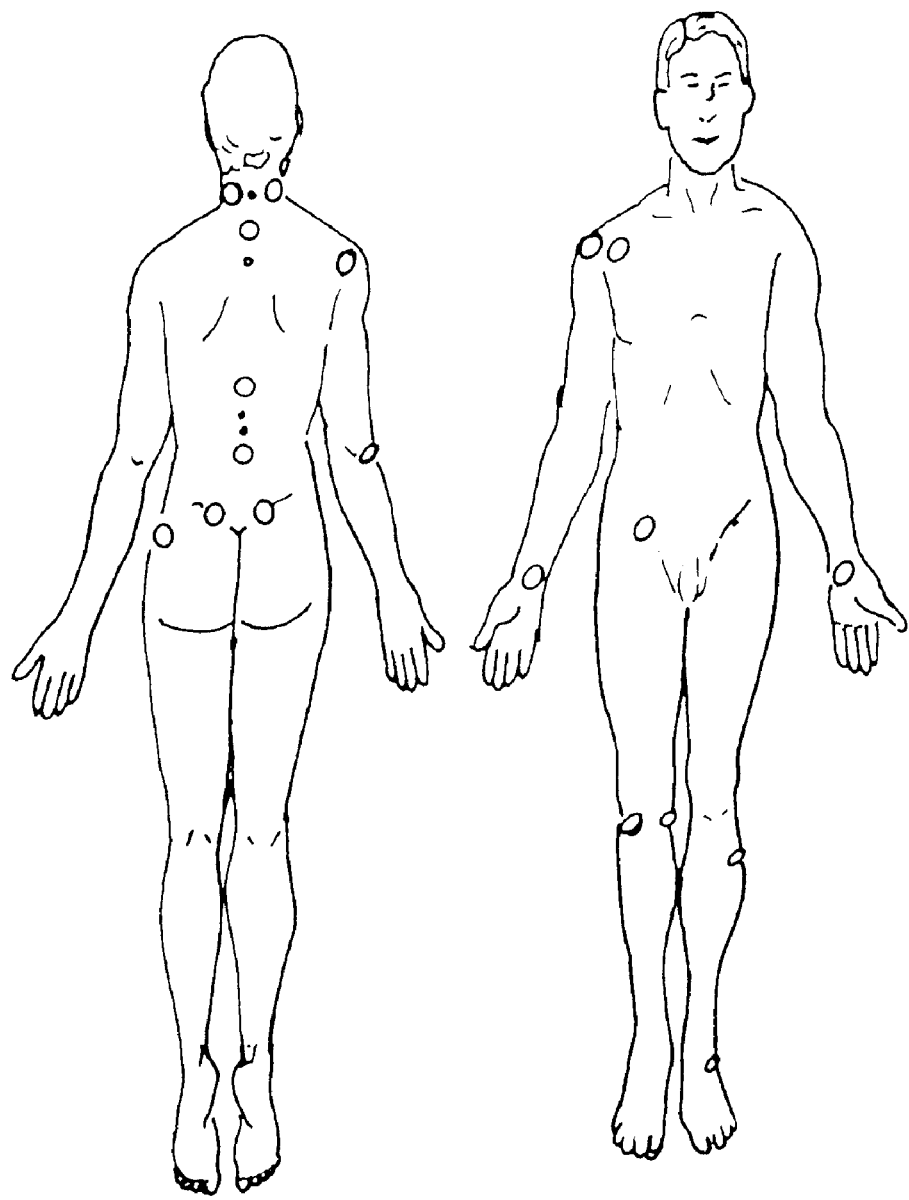
Figure 24:
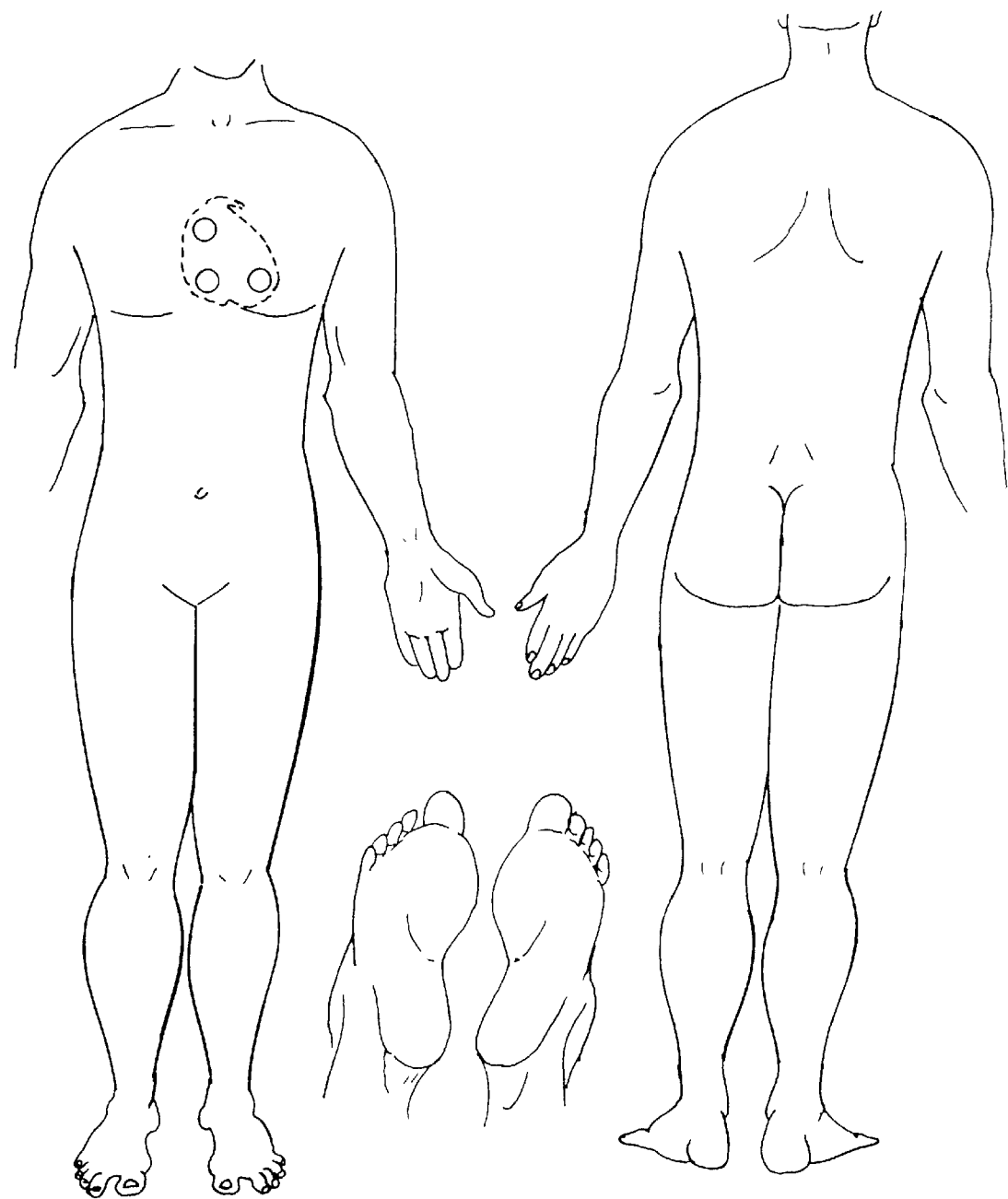

FIG. 7 shows fitment designs with location of the treatment devices for mild to moderate knee pain;

FIG. 8 shows view of a knee fitment for treatment of more severe knee pain and inflammation;

FIG. 9 shows placement of the magnetic treatment devices of the invention for hip, joint and muscle pain;

FIG. 10a shows placement for the magnetic generator in the fitment for moderate elbow pain;

FIG. 10b shows placement of the magnetic generator in the fitment with proper placement for elbow pain with joint and tendon involvement;

FIG. 11a shows placement of the magnetic devices in a fitment for wrist pain and especially overuse or Carpel Tunnel Syndrome;

FIG. 11b shows placement of the magnetic device in an alternate fitment for wrist pain and especially overuse or Carpel Tunnel Syndrome;

FIG. 11c shows placement of the magnetic device directly over the skin via a double adhesive sticker for wrist pain and especially for overuse or Carpel Tunnel Syndrome;

FIG. 12 shows placement for shoulder pain of the joint and surrounding tissues from such conditions as arthritis;

FIG. 13 shows placement of the magnetic device of the invention on one area of potential injury of the rotator cuff of the shoulder;

FIG. 14 shows placement and design of the magnetic device of the invention in a helmet fitment for treatment of maladies of the head both bone and soft tissue. i.e., nervous system structures;

FIG. 15 shows alternate design of FIG. 14;

FIG. 16 shows alternate design of FIG. 14;

FIG. 17 shows alternate design of FIG. 14;

FIG. 18 shows alternate design of FIG. 14;

FIG. 19 shows alternate design of FIG. 14;

FIG. 20 shows cutaway view of FIG. 19;

FIG. 21 shows views of tailored back fitment;

FIG. 22 shows views of tailored knee fitment;

FIG. 23 shows views of common placements for specific maladies of the neck, shoulder, elbow, back, hip, knee and ankle;

FIG. 24 shows attachment to the chest wall of devices to cover specific areas of the myocardium by the magnetic flux field for treatment of rhythm disturbance and pain of angina.

BEST MODE(S) FOR CARRYING OUT THE INVENTION

Figure 1:
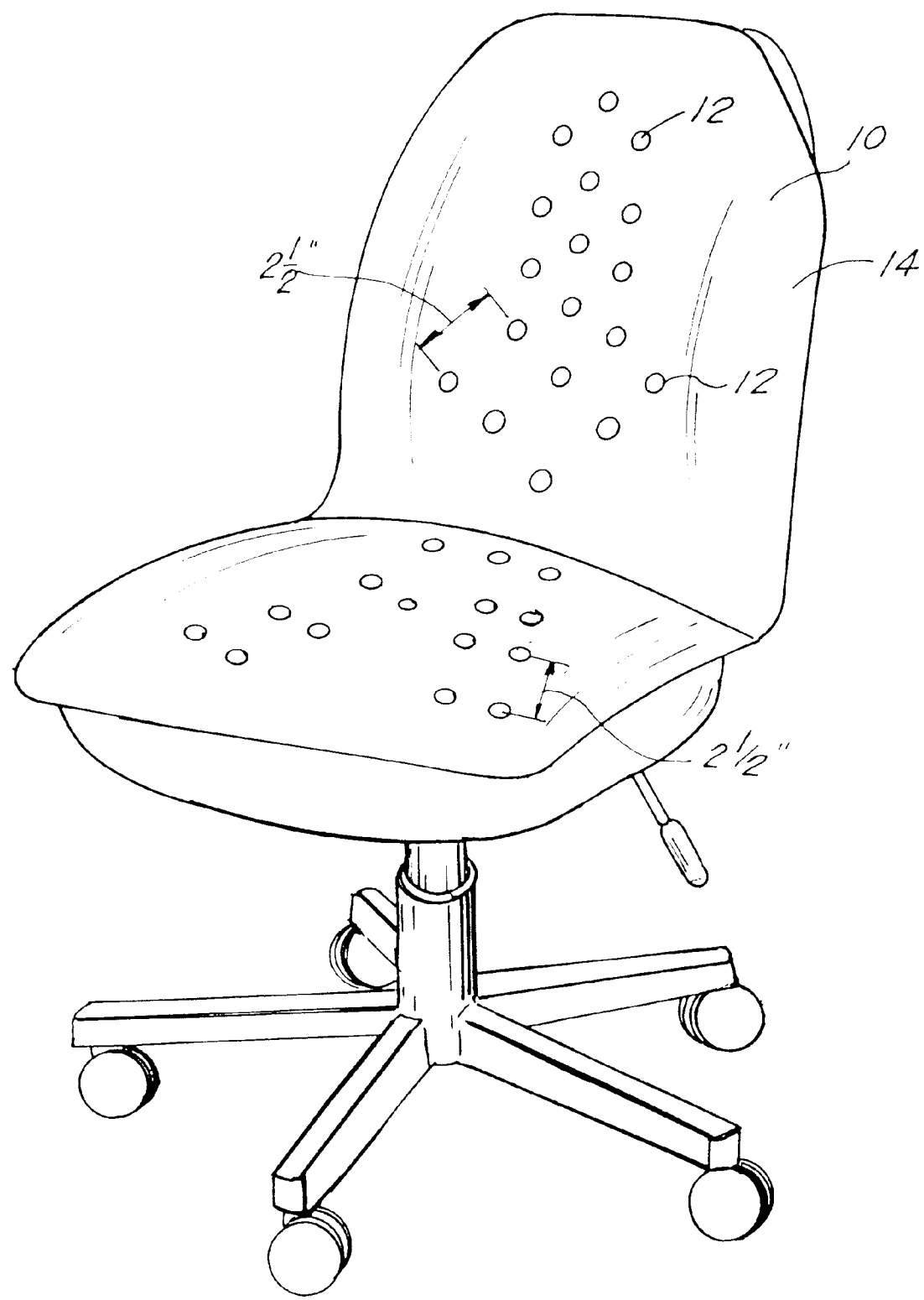
FIG. 1 is a perspective view of a seat cushion having magnetic devices securely positioned therein, which is placed in a chair.

FIG. 1 shows a seat comforter containing a plurality of magnetic devices 12 which are secured therein. The seat comforter 10 has a back portion 14 and a seat portion 16. Other magnetic devices may also be used rather than the Magna Bloc™ therapeutic devices; however, their use is not preferred. The magnetic devices 12 ideally produce a magnetic field with high magnetic flux gradient to alter the firing of impulses from pain sensing fibers. The magnet device 12 contains four magnetic bodies arranged in alternating polarity. A containment device, such as a hard plastic shell, a vacuum-sealed pouch, foam or soft carrier material may be used to carry those four magnetic bodies.

FIGS. 2 and 3 show a user wearing a pair of tights 40 with magnetic devices 12. The orientation of magnetic device 12 enhances blood flow and provides pain/discomfort relief during physical exertion.

Figure 4:
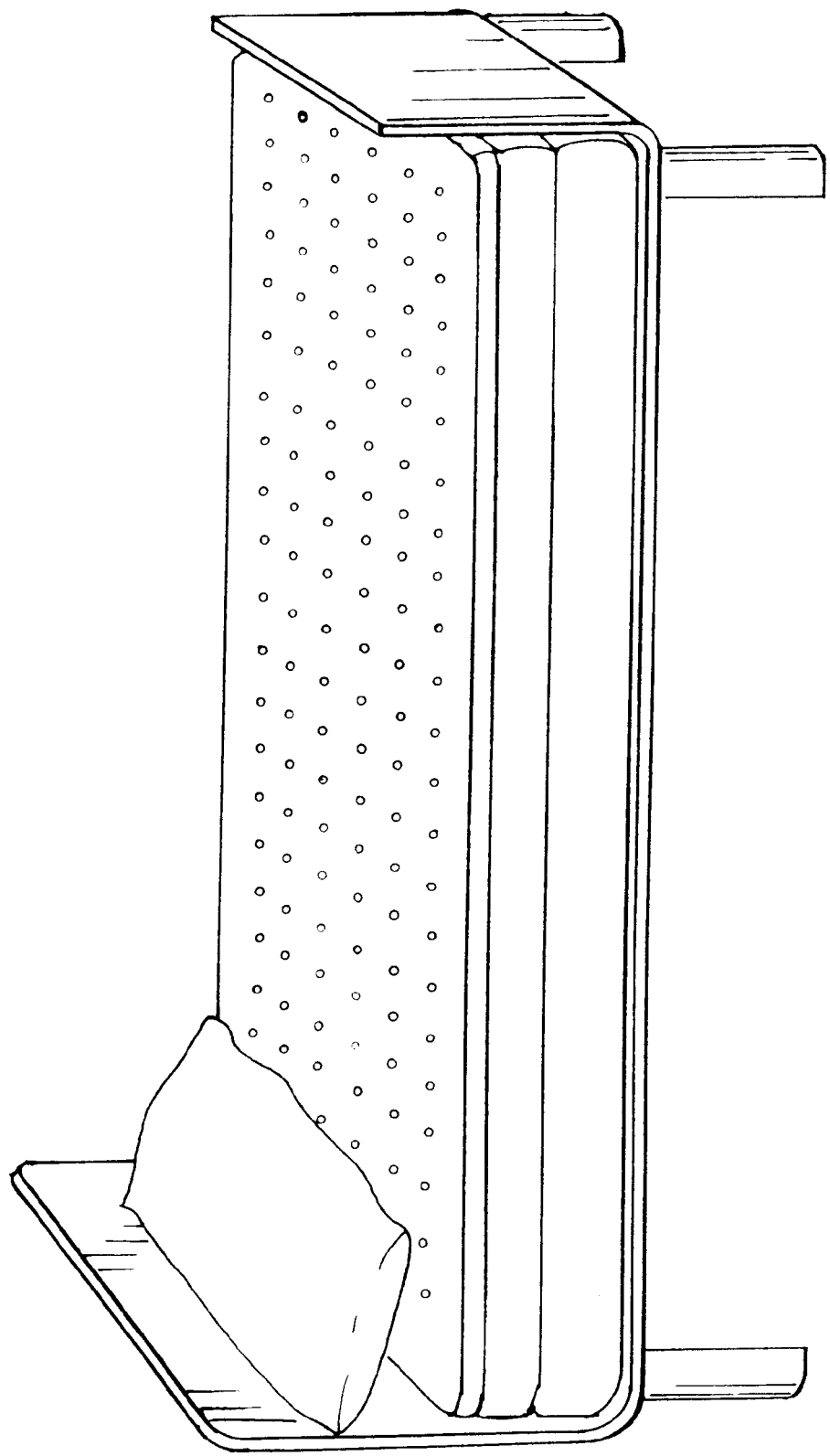
FIG. 4 is a perspective view of a comforter with magnetic devices secured therein resting upon a bed.

FIG. 4 shows a comforter 70 with magnetic devices 12 embedded or sewn therein. Any method of securing the magnetic devices 12 in comforter 70 to prevent relative movement may be used. In the preferred embodiment, the magnetic devices 12 may be vacuumed packed into plastic sleeves and sewn into a cloth material to create comforter 70. The magnetic devices 12 are arranged in a rectangular array in this preferred embodiment. However, any arrangement, which generally evenly disperses magnetic devices 12, may be used.

Figure 5A:
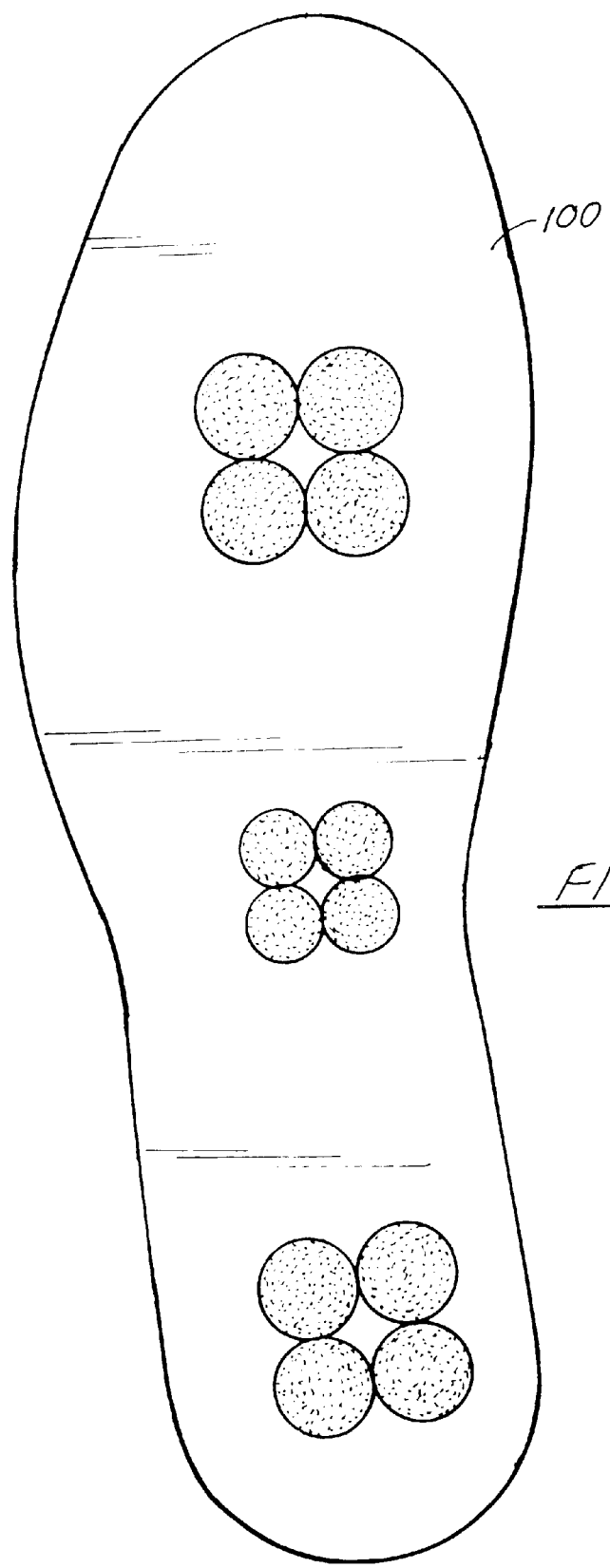
FIG. 5a is a top view of an insole, which has a plurality of magnetic devices therein at areas of major stress in the foot at areas of major stress in the foot.
Figure 5B:
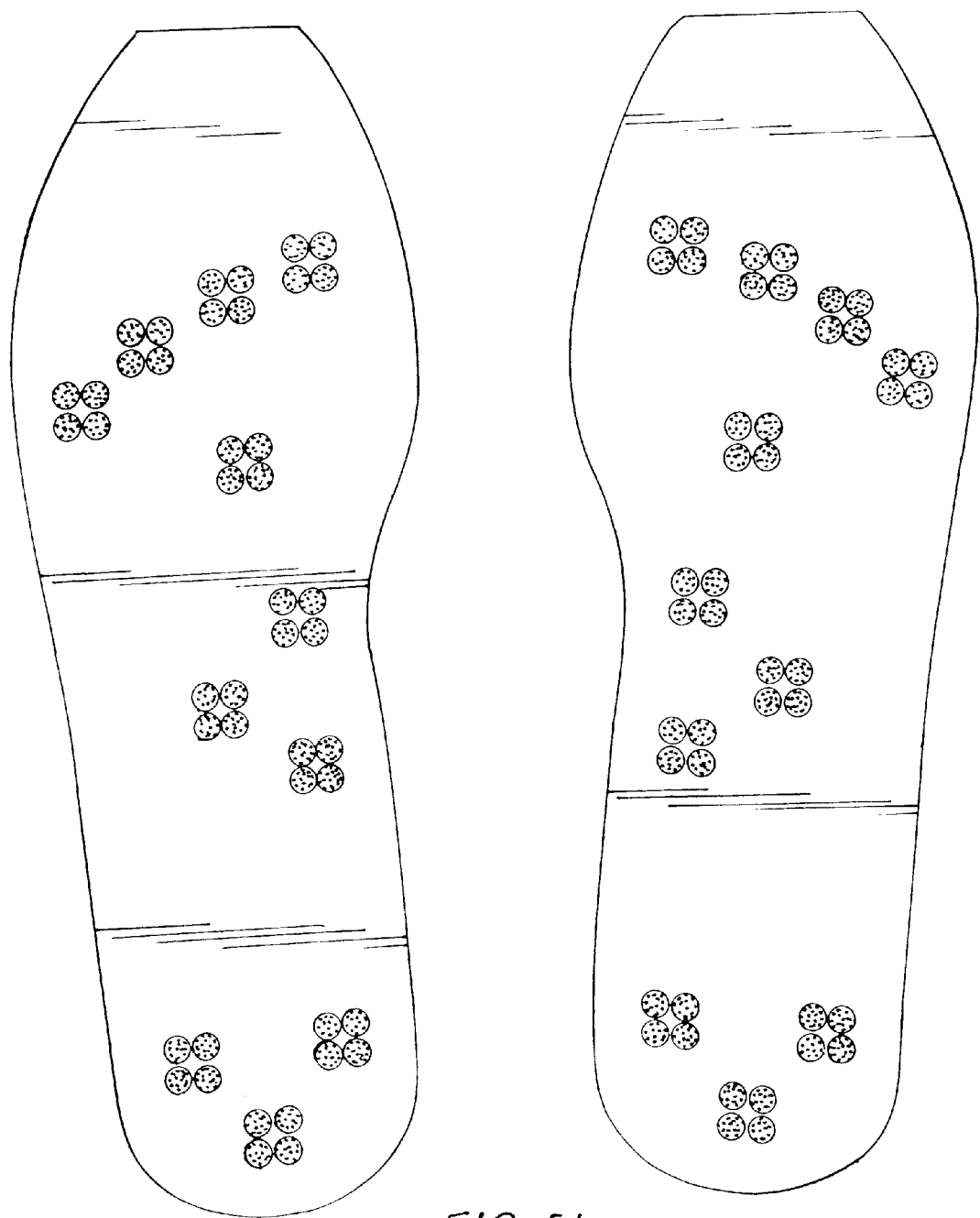
FIG. 5b is an alternate view of a duster of smaller devices clustered in the area of major stress in the foot.

FIG. 5 shows an insole 100 with a magnetic device 12 secured therein. Preferably, 3 magnetic devices 12 are used. Use of more or fewer number of magnetic devices 12 is believed to be less effective in treating foot pain or discomfort, but may be advantageous for reasons of flexibility.

Figure 6A:
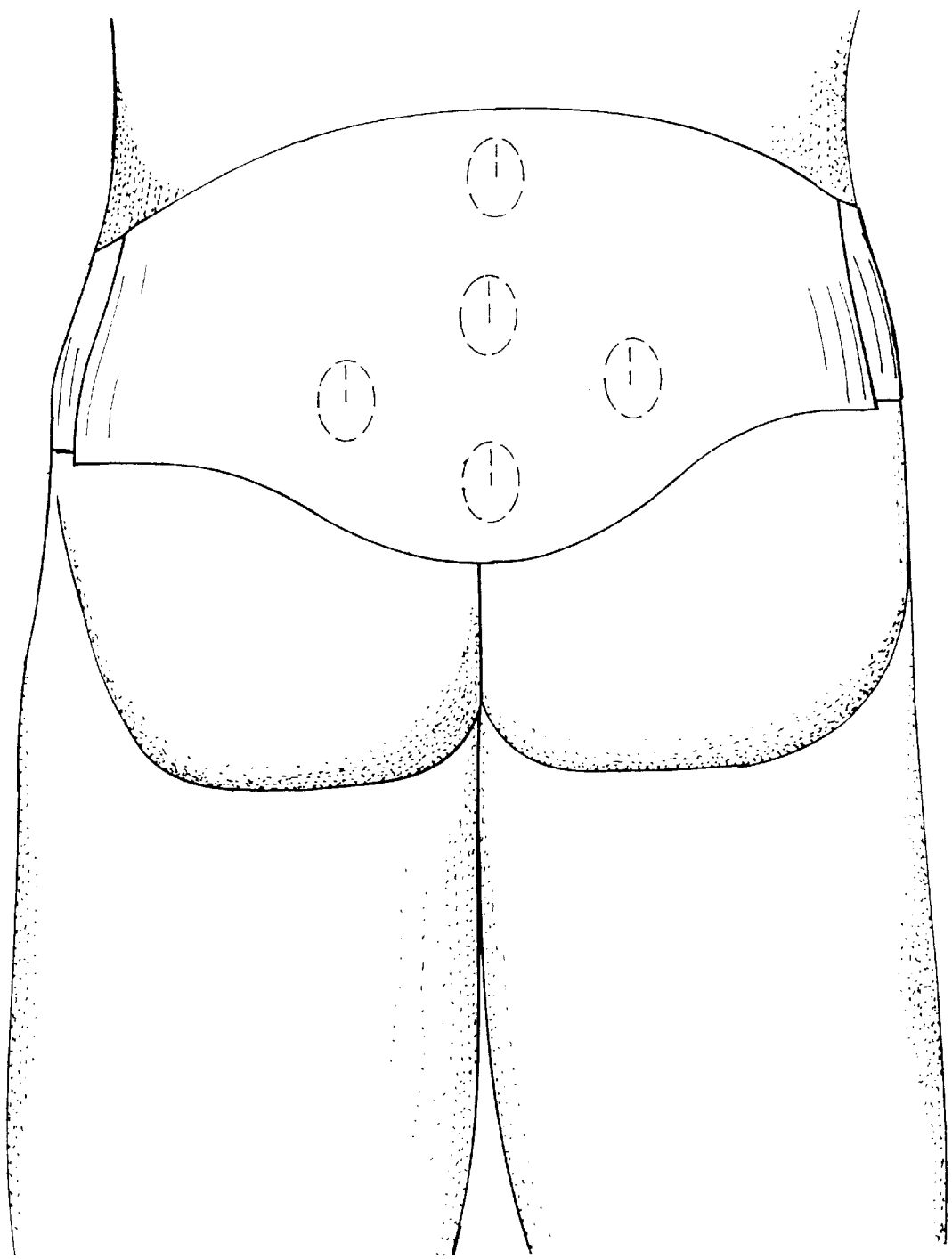
FIG. 6a shows views of a back fitment using magnet devices and fitments with fasteners to allow each magnetic device to be individually located on the fitment to allow customization for different users.
Figure 6B:
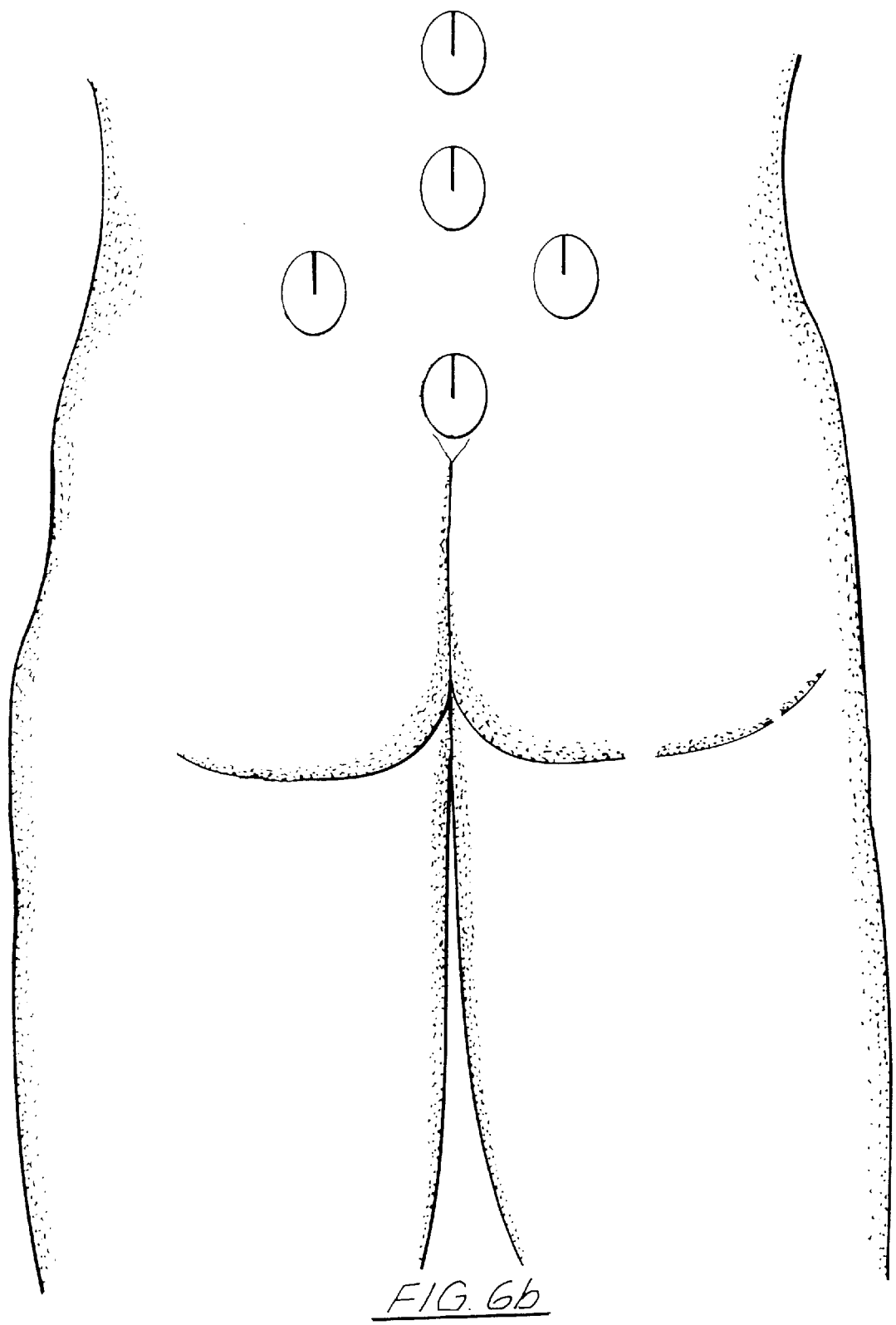
FIG. 6b is an array of locations attached directly to the skin for lower back pain and nerve root inflammation or compression.

FIGS. 6a and 6b show the proper placement of the magnetic flux field generators for low back pain and/or radicular pain originating in neuronal and non-neuronal structures of the back with the final common pain pathway being stimulation of a pain sensing fiber.

FIG. 7 reveals the placement of the magnetic flux field generators over the knee joint for treatment of pain and inflammation.

FIG. 8 reveals the placement of the magnetic flux field generators over the knee joint and the infra patellar and supra patellar bursa for treatment of more severe cases of pain and inflammation.

FIG. 9 reveals the placement of the magnetic flux field generators over the hip joint and surrounding soft tissue for treatment of pain and inflammation of the joint space or surrounding soft tissue.

FIG. 10a reveals the placement of the magnetic flux field generators over the elbow joint for treatment of pain and inflammation of the joint space and surrounding soft tissue.

FIG. 10b reveals the placement of the magnetic flux field generators over the elbow and common points of tendon inflammation in painful and inflammatory conditions of the elbow and forearm.

FIG. 11a reveals the placement of the magnetic flux field generator over the area of the carpel tunnel of the wrist for painful and/or overused wrist such as Carpel Tunnel Syndrome.

FIG. 11b reveals the placement of the magnetic flux field generator using an alternative embodiment over the area of the carpel tunnel of the wrist for painful and/or overused wrist such as in Carpel Tunnel Syndrome.

FIG. 11c reveals the placement of the magnetic flux field generator attached over the area of the carpel tunnel with a double adhesive device.

FIG. 12 reveals the placement of the magnetic flux field generator devices over the shoulder joint and. soft tissues for treatment of conditions such as arthritis.

FIG. 13 reveals the placement of the devices over a rotator cuff area for an example of treatment of a rotator cuff tear.

FIGS. 14–20 reveal attachment means and placement of the magnetic flux field generators of the invention for treatment of maladies of the head, both bony and soft tissue, such as nervous system disorders.

The above placement or positioning of magnetic devices as shown in FIGS. 1–24 are believed to provide superior pain or discomfort relief relative to prior art magnetic devices and their positioning. Double side adhesive tape or fitments may be used to secure the magnetic device 12 in the described positions and in the prescribed arrangements.

Also disclosed is a method of arranging magnetic devices 12 in a fitment. A physician or user first determines the number and placement of magnetic devices relative to body locations, such as the lower back. No one single fitment and magnetic devices design will work for an users as users come in all sizes. Rather, it may be more effective to custom place each magnetic device in its most effective location on the body. After these locations are determined, the magnetic devices are removed relative to the body. Next a carrier fitment is applied over the body part to be treated. Ideally one or both of the fitments or the magnetic devices have means for reversibly securing the magnetic device relative to the fitment For example, the magnetic device end fitment could have cooperating hook and loop fasteners. The magnetic devices are attached to the fitment such that each magnetic device is placed at its predetermined optimal position to insure optimal efficacy for the combination of the fitment and magnetic devices. Although not preferred, the magnetic devices could also be permanently attached to the fitment, such as by the use of permanent adhesive such as glue or rubber cement.

FIG. 21-1 shows an exemplary back fitment 100. Magnetic devices 102 with hooks 10 secured thereto are shown in FIG. 21-2. FIG. 21-3 shows an ideal general arrangement of the magnetic devices 102 being applied to a patient's back using double sided tape. A total of five magnetic devices 102 are applied in this exemplary case as best meet the needs of the patent. The fitment 100 is pressed against the patient's back with the hook and loop fasteners holding this magnetic device 102 to fitment 100. An interior cloth piece 110 is applied over the exposed magnetic device 102 and secures to fitment 100 to provide better securment and to provide a barrier to hook or loops on fitment 100. Otherwise, the hook and loop material might scratch or otherwise irritate the patients skin.

The placement number of cooperating magnetic devices and geometrical arrangement of the magnetic devices on patient's body parts, i.e. wrist, back. neck, head, knee (see FIG. 22), et cetra, has been developed through years of clinical studies, basic science research, clinical trial and error, and patient feedback. This application is intended to disclose this accumulated knowledge in the optimal treatment of pain and discomfort at different body locations using superior magnetic devices. The accompanying drawings describe the placement of magnets with the desired gradient, for use in the treatment of various human and/or animal maladies, regardless of the magnetic and/or electro magnetic generator source which produces the desired gradient.

FIG. 23 depicts placement of the flux field generators in strategic location for the common aches and pains of daily living. These pains may be secondary to structural or inflammatory changes but the discomfort has a final common pathway, i.e., by orientation of pain sensing fibers.

FIG. 24 represents strategic placement of the magnetic flux field generator devices over the anterior myocardium for the relief of angina pectoris and/or rhythm disturbance.

What is claimed is:

1. A method of arranging a plurality of therapeutic electromagnetic treatment devices in a fitment, comprising the following steps:
    a) providing a plurality of the therapeutic electromagnetic treatment devices, each device further comprising a plurality of electromagnetic bodies each body comprising a plurality of magnetic poles substantially in a single plane, at least one of the magnetic poles having secured a ferroconductor flux return ring thereto for increasing the strength and gradient without altering the centered charge and symmetry of the three dimensional radiant magnetic flux field;
    b) orienting the magnetic bodies to define four vertices of a quadrilateral shape, and each having magnetic poles exerting magnetic force on the other plurality of magnetic poles;
    c) providing a fitment for accommodating the electromagnetic treatment device; and
    d) placing the fitment containing the treatment device on a part of the human body so that a flux field created by the plurality of electromagnetic bodies interacts with damaged tissue to re-establish normal physiological functioning of the tissue.

2. A device for interacting with the body of living organisms, comprising:
    a) an electromagnetic treatment device comprising a plurality of electromagnetic bodies, each body including a plurality of magnetic poles substantially in a single plane;
    b) the magnetic bodies being oriented to define four vertices of a quadrilateral shape and each of the magnetic poles exerting a magnetic force on other plurality of magnetic poles when the poles are electrically charged;
    c) a ferroconductor flux return ring secured to at least one of the poles for increasing the strength and gradient without altering a centered charge and symmetry of any three dimensional steep radiant magnetic flux field;
    d) a containment component for holding the magnetic poles of the magnetic bodies in the orientation; and
    e) a fitment accommodating a plurality of electromagnetic treatment devices, which when placed on a portion of the human body having damaged tissue, a flux field created by the electromagnetic devices interacts with the damaged tissue to re-establish normal physiological functioning of the tissue.

3. The apparatus of claim 2, wherein the device would be attached over the area of the carpal tunnel with a double adhesive fitment.

4. The apparatus of claim 2 wherein the device in the fitment would be positioned over the soft tissues for treatment of conditions including arthritis.

* * * * *